(12) United States Patent
Kim

(10) Patent No.: US 10,034,643 B2
(45) Date of Patent: Jul. 31, 2018

(54) APPARATUS AND METHOD FOR ORDERING IMAGING OPERATIONS IN AN X-RAY IMAGING SYSTEM

(71) Applicant: SAMSUNG ELECTRONICS CO., LTD., Suwon-si (KR)

(72) Inventor: Sang-uk Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 270 days.

(21) Appl. No.: 15/098,838

(22) Filed: Apr. 14, 2016

(65) Prior Publication Data

US 2016/0310098 A1 Oct. 27, 2016

(30) Foreign Application Priority Data

Apr. 22, 2015 (KR) ........................ 10-2015-0056886

(51) Int. Cl.
*A61B 6/00* (2006.01)
*G01T 1/16* (2006.01)

(52) U.S. Cl.
CPC .............. *A61B 6/469* (2013.01); *A61B 6/461* (2013.01); *A61B 6/5241* (2013.01); *A61B 6/542* (2013.01); *A61B 6/544* (2013.01); *A61B 6/4233* (2013.01); *A61B 6/467* (2013.01); *A61B 6/5235* (2013.01); *A61B 6/54* (2013.01)

(58) Field of Classification Search
CPC .... A61B 6/00; A61B 6/42; A61B 6/46; A61B 6/461; A61B 6/463; A61B 6/465; A61B 6/467; A61B 6/469; A61B 6/48; A61B 6/486; A61B 6/52; A61B 6/5211; A61B 6/5235; A61B 6/5241; A61B 6/54; A61B 6/542; A61B 6/544
See application file for complete search history.

(56) References Cited

U.S. PATENT DOCUMENTS

| 6,208,710 | B1 * | 3/2001 | Nagai | A61B 6/00 378/108 |
| 7,555,100 | B2 | 6/2009 | Wang et al. | |
| 7,978,816 | B2 * | 7/2011 | Matsuura | A61B 6/032 378/62 |

* cited by examiner

*Primary Examiner* — Anastasia Midkiff
(74) *Attorney, Agent, or Firm* — Staas & Halsey LLP

(57) ABSTRACT

An X-ray apparatus and system are capable of preventing possible generation of after-images and ghost images due to partial imaging of an object by determining an order of imaging operations with respect to a plurality of partial X-ray imaging regions based on size information about portions of the object respectively represented on the plurality of partial X-ray imaging regions.

20 Claims, 24 Drawing Sheets

APPARATUS AND METHOD FOR ORDERING IMAGING OPERATIONS IN AN X-RAY IMAGING SYSTEM

CROSS-REFERENCE TO RELATED APPLICATIONS

This application claims the priority benefit of Korean Patent Application No. 10-2015-0056886, filed on Apr. 22, 2015, in the Korean Intellectual Property Office, the disclosure of which is incorporated herein in its entirety by reference.

BACKGROUND

1. Field

The following description relates to X-ray apparatuses and systems, and more particularly, to X-ray apparatuses and systems capable of preventing generation of after-images due to partial X-ray imaging.

2. Description of the Related Art

X-rays are electromagnetic waves having wavelengths of 0.01 to 100 angstroms (A), and are widely used in medical apparatuses for imaging the inside of a living body or non-destructive testing equipment for industrial use due to their ability to penetrate objects.

An X-ray apparatus using X-rays may obtain X-ray images of an object by transmitting X-rays emitted from an X-ray source through an object and detecting a difference in intensities of the transmitted X-rays via an X-ray detector. The X-ray images may be used to examine an internal structure of an object and diagnose a disease of the object. The X-ray apparatus facilitates observation of an internal structure of an object by using a principle in which penetrating power of an X-ray varies depending on the density of the object and atomic numbers of atoms constituting the object. As a wavelength of an X-ray decreases, penetrating power of the X-ray increases and a screen becomes brighter.

SUMMARY

The following description relates to X-ray apparatuses and systems capable of preventing generation of after-images due to partial X-ray imaging.

Additional aspects will be set forth in part in the description which follows and, in part, will be apparent from the description, or may be learned by practice of the presented embodiments.

According to an aspect of an embodiment, an X-ray apparatus for obtaining an X-ray image by stitching a plurality of partial images of the object together includes: an input interface configured to receive a first user input for setting an imaging area with respect to the object; a controller configured to divide the imaging area set according to the received user input into a plurality of partial X-ray imaging regions and determine an order of imaging operations with respect to the plurality of partial X-ray imaging regions based on size information about portions of the object represented on the plurality of partial X-ray imaging regions; and an X-ray radiator configured to radiate X-rays onto the plurality of partial X-ray imaging regions according to the determined order in order to perform partial imaging of the object.

The controller may determine the order of the imaging operations as being an order from a partial X-ray imaging region where a portion of the object having a large area or width is represented on a partial X-ray imaging region where a portion of the object having a small area or width is represented.

The controller may acquire one of representative values including an average value, a minimum value, a median value, and a maximum value of widths of a portion of the object represented on each of the plurality of partial X-ray imaging regions and determines the order of the imaging operations with respect to the plurality of partial X-ray imaging regions based on the acquired one of the representative values.

The controller may measure the widths of the portion of the object represented on each of the plurality of partial X-ray imaging regions at predetermined sampling intervals arranged in a vertical direction and acquires a representative value of widths in a horizontal direction of the object based on the measured widths of the portions of the object.

The X-ray apparatus may include an image acquisitioner configured to acquire a photographic image by photographing the object, and the controller may acquire information about areas of the portions of the object respectively represented on the plurality of partial X-ray imaging regions, based on the acquired photographic image.

The X-ray apparatus may further include a storage configured to store standard body dimension information of the object including information about widths of the portions of the object. The controller may acquire information about the widths of the portions of the object respectively represented on the plurality of partial X-ray imaging regions based on the standard body dimension information of the object and determines the order of the imaging operations with respect to the plurality of partial X-ray imaging regions based on the acquired information.

The controller may determine the order of the imaging operations with respect to the plurality of partial X-ray imaging regions based on a size of areas of the portions of the object respectively represented on the plurality of partial X-ray imaging regions and a path of movement of the X-ray radiator.

The controller may detect a change in a direction of movement of the X-ray radiator, determine, if there is a change in the direction of movement of the X-ray radiator, whether a difference between areas of portions of the object respectively represented on partial X-ray imaging regions related to the change in the direction of movement of the X-ray radiator from among the plurality of partial X-ray imaging region is less than or equal to a threshold value, and change the order of the imaging operations with respect to the partial X-ray imaging operations if the difference is less than or equal to the threshold value.

The X-ray apparatus may further include an output interface configured to display information representing the order of the imaging operations with respect to the plurality of partial X-ray imaging regions and being determined by the controller. The input interface may receive a second user input for approving or changing the determined order of the imaging operations, and the controller may determine again the order of the imaging operations with respect to the plurality of partial X-ray imaging regions based on the second user input.

The controller may obtain an X-ray image of the object by stitching together a plurality of partial X-ray images acquired by performing the imaging operations in the determined order.

According to an aspect of an embodiment, a method of obtaining an X-ray image by stitching together a plurality of partial images of the object includes: receiving a first user input for setting an imaging area with respect to the object; dividing the imaging area set according to the received user input into a plurality of partial X-ray imaging regions; and determining an order of imaging operations with respect to the plurality of partial X-ray imaging regions based on size information about a portions of the object represented on the plurality of partial X-ray imaging regions.

The determining of the order of the imaging operations may include determining the order of imaging operation as being an order from a partial X-ray imaging region where a portion of the object having a large area or width is represented on a partial X-ray imaging region where a portion of the object having a small area or width is represented.

The determining of the order of the imaging operations may include: acquiring one of representative values including an average value, a minimum value, a median value, and a maximum value of widths of a portion of the object represented on each of the plurality of partial X-ray imaging regions; and determining the order of the imaging operations with respect to the plurality of partial X-ray imaging regions based on the acquired one of the representative values.

The widths of the portion of the object represented on each of the plurality of partial X-ray imaging regions may be measured at predetermined sampling intervals arranged in a vertical direction, and the representative value may be acquired based on the measured widths of the portion of the object.

The determining of the order of the imaging operations may include acquiring information about areas of the portions of the object respectively represented on the plurality of partial X-ray imaging regions by photographing the object and determining the order of the imaging operations with respect to the plurality of partial X-ray imaging regions based on the acquired information.

The determining of the order of the imaging operations may include acquiring standard body dimension information of the object including information about widths of the portions of the object and determining the order of the imaging operations with respect to the plurality of partial X-ray imaging regions based on the acquired standard body dimension information.

The determining of the order of the imaging operations may include determining the order of imaging operations with respect to the plurality of partial X-ray imaging regions based on a size of areas of the portions of the object respectively represented on the plurality of partial X-ray imaging regions and a direction of movement of an X-ray radiator configured to radiate X-rays onto the plurality of partial X-ray imaging regions in order to perform partial imaging of the object.

The determining of the order of the imaging operations may include: detecting a change in a direction of movement of the X-ray radiator; determining, if there is a change in the direction of movement of the X-ray radiator, whether a difference between areas of portions of the object respectively represented on partial X-ray imaging regions related to the change in the direction of movement of the X-ray radiator from among the plurality of partial X-ray imaging region is less than or equal to a threshold value; and changing the order of the imaging operations with respect to the partial X-ray imaging operations if the difference is less than or equal to the threshold value.

The method may further include: displaying the determined order of the imaging operations on an output interface; receiving a second user input for approving or changing the determined order of the imaging operations displayed on the output interface; and determining again the order of the imaging operations with respect to the plurality of partial X-ray imaging regions based on the second user input.

The method may further include obtaining an X-ray image of the object by stitching together a plurality of partial X-ray images acquired by performing the imaging operations in the determined order.

According to an aspect of an embodiment, a non-transitory computer-readable recording medium has recorded thereon a program for executing the above method on a computer

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
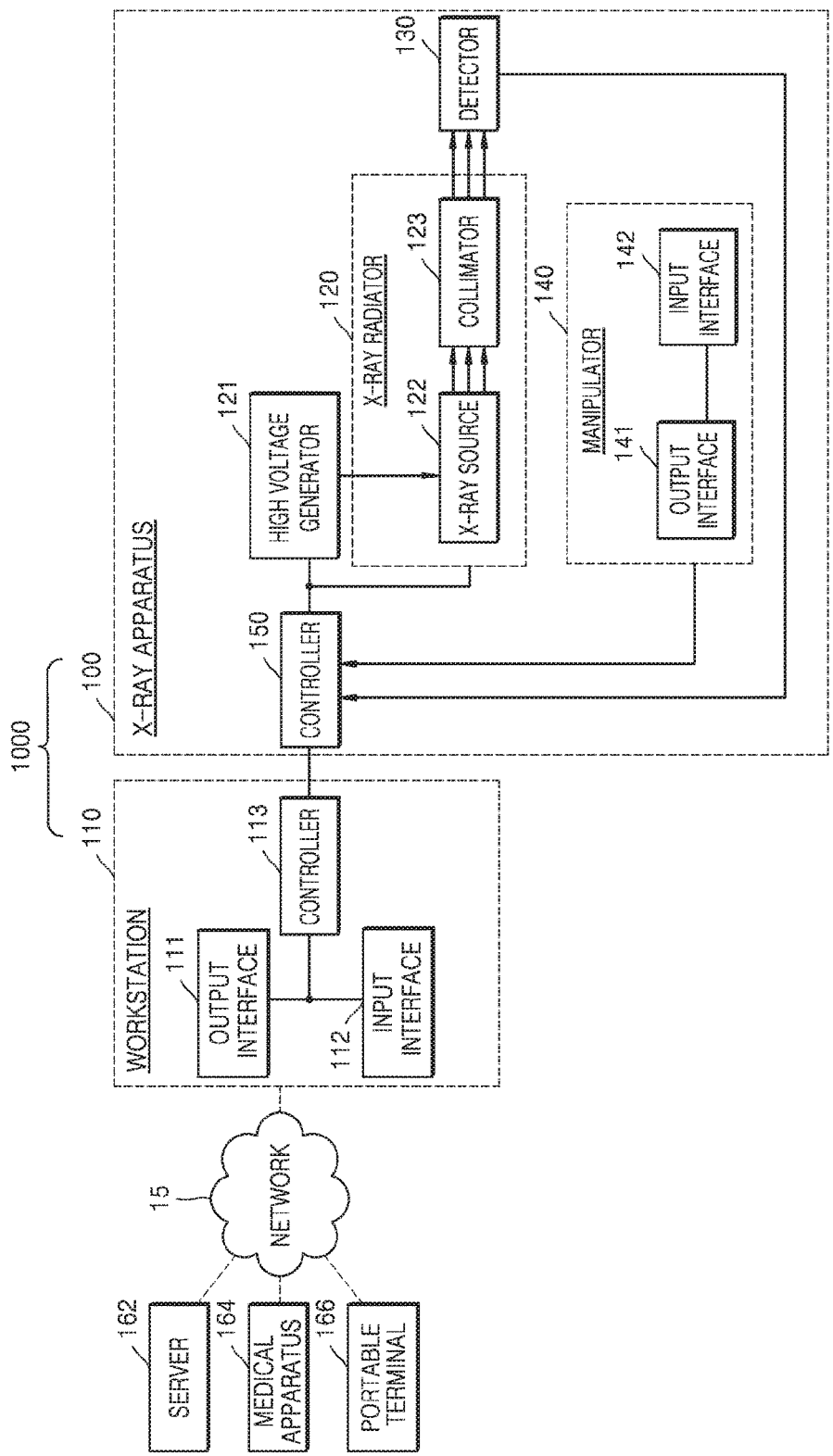
FIG. 1 is a block diagram of a configuration of an X-ray system.

Reference will now be made in detail to the embodiments, examples of which are illustrated in the accompanying drawings, wherein like reference numerals refer to like elements throughout. The embodiments are described below to explain the present disclosure by referring to the figures.

The attached drawings for illustrating embodiments of the present disclosure are referred to in order to gain a sufficient understanding of the present disclosure, the merits thereof, and the objectives accomplished by the implementation of the present disclosure. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present disclosure will only be defined by the appended claims.

Hereinafter, the terms used in the specification will be briefly described, and then the present disclosure will be described in detail.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the present disclosure. Expressions such as "at least one of," when preceding a list of elements, modify the entire list of elements and do not modify the individual elements of the list.

Throughout the specification, an "image" may denote multi-dimensional data composed of discrete image elements (for example, pixels in a two-dimensional image and voxels in a three-dimensional image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

In addition, an "object" may be a human, an animal, or a part of a human or animal. For example, the object may include an organ (for example, the liver, the heart, the womb, the brain, breasts, or the abdomen), blood vessels, or a combination thereof. The object may be a phantom. The phantom denotes a material having a volume, a density, and an effective atomic number that are approximately the same as those of a living organism. For example, the phantom may be a spherical phantom having similar properties to those of the human body.

Throughout the specification, a "user" may be, but is not limited to, a medical expert, for example, a medical doctor, a nurse, a medical laboratory technologist, or a medical imaging expert, or a technician who repairs medical apparatuses.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest imaging, simple abdomen imaging, simple skeleton imaging, simple nasal sinuses imaging, simple neck soft tissue imaging, and breast imaging.

FIG. 1 is a block diagram of an X-ray system 1000.

Referring to FIG. 1, the X-ray system 1000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray radiator 120, a high voltage generator 121, a detector 130, a manipulator 140, and a controller 150. The controller 150 may control overall operations of the X-ray apparatus 100.

The high voltage generator 121 generates a high voltage for generating X-rays, and applies the high voltage to an X-ray source 122.

The X-ray radiator 120 includes the X-ray source 122 receiving the high voltage from the high voltage generator 121 to generate and radiate X-rays, and a collimator 123 for guiding a path of the X-ray radiated from the X-ray source 122 and adjusting an irradiation region radiated by the X-ray.

The X-ray source 122 includes an X-ray tube that may be realized as a vacuum tube diode including a cathode and an anode. An inside of the X-ray tube is set as a high vacuum state of about 10 mmHg, and a filament of the anode is heated to a high temperature to generate thermal electrons. The filament may be a tungsten filament, and a voltage of about 10V and a current of about 3 to 5 A may be applied to an electric wire connected to the filament to heat the filament.

In addition, when a high voltage of about 10 to about 300 kVp is applied between the cathode and the anode, the thermal electrons are accelerated to collide with a target material of the cathode, and then, an X-ray is generated. The X-ray is radiated outside via a window, and the window may be formed of a beryllium thin film. In this case, most of the energy of the electrons colliding with the target material is consumed as heat, and remaining energy is converted into the X-ray.

The cathode is mainly formed of copper, and the target material is disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, an energy of the X-ray (energy of photon) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detector 130 detects an X-ray that is radiated from the X-ray radiator 120 and has been transmitted through an object. The detector 130 may be a digital detector. The detector 130 may be implemented by using a thin film transistor (TFT) or a charge coupled device (CCD). Although the detector 130 is included in the X-ray apparatus 100 in FIG. 1, the detector 130 may be an X-ray detector that is a separate device capable of being connected to or separated from the X-ray apparatus 100.

The X-ray apparatus 100 may further include a manipulator 140 for providing a user with an interface for manipulating the X-ray apparatus 100. The manipulator 140 may include an output unit 141 and an input unit 142. The input unit 142 may receive from a user a command for manipulating the X-ray apparatus 100 and various types of information related to X-ray imaging. The controller 150 may control or manipulate the X-ray apparatus 100 according to the information received by the input unit 142. The output unit 141 may output sound representing information related to an imaging operation such as the X-ray radiation under the control of the controller 150.

The workstation 110 and the X-ray apparatus 100 may be connected to each other by wire or wirelessly. When they are connected to each other wirelessly, a device (not shown) for synchronizing clock signals with each other may be further included. The workstation 110 and the X-ray apparatus 100 may exist within physically separate spaces.

The workstation 110 may include an output unit 111, an input unit 112, and a controller 113. The output unit 111 and the input unit 112 provide a user with an interface for manipulating the workstation 110 and the X-ray apparatus 200. The controller 113 may control the workstation 110 and the X-ray apparatus 200.

The X-ray apparatus 100 may be controlled via the workstation 110 or may be controlled by the controller 150 included in the X-ray apparatus 100. Accordingly, a user may control the X-ray apparatus 100 via the workstation 110 or may control the X-ray apparatus 100 via the manipulator 140 and the controller 150 included in the X-ray apparatus 100. In other words, a user may remotely control the X-ray apparatus 100 via the workstation 110 or may directly control the X-ray apparatus 100.

Although the controller 113 of the workstation 110 is separate from the controller 150 of the X-ray apparatus 100 in FIG. 1, FIG. 1 is only an example. In some embodiments, the controllers 113 and 150 may be integrated into a single controller, and the single controller may be included in only one of the workstation 110 and the X-ray apparatus 100. Hereinafter, the controllers 113 and 150 may denote the controller 113 of the workstation 110 and/or the controller 150 of the X-ray apparatus 100.

The output unit 111 and the input unit 112 of the workstation 110 may provide a user with an interface for manipulating the X-ray apparatus 100, and the output unit 141 and the input unit 142 of the X-ray apparatus 100 may also provide a user with an interface for manipulating the X-ray apparatus 100. Although the workstation 110 and the X-ray radiation apparatus 100 include the output units 111 and 141, respectively, and the input units 112 and 142, respectively, in FIG. 1, embodiments are not limited thereto. Only one of the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include a keyboard, a mouse, a touch screen, a voice recognizer, a fingerprint recognizer, an iris recognizer, and other input devices which are well known to one of ordinary skill in the art. The user may input a command for radiating the X-ray via the input units 112 and 142, and the input units 112 and 142 may include a switch for inputting the command. The switch may be configured so that a radiation command for radiating the X-ray may be input only when the switch is pushed in two steps.

In other words, when the user pushes the switch, a prepare command for performing a pre-heating operation for X-ray radiation may be input, and in this state, when the user pushes the switch deeper, a radiation command for performing substantial X-ray radiation may be input. When the user manipulates the switch as described above, the controllers 113 and 150 generate signals corresponding to the commands input through the switch manipulation, that is, a prepare signal, and transmit the generated signals to the high voltage generator 121 generating a high voltage for generating the X-ray.

When the high voltage generator 121 receives the prepare signal from the controllers 113 and 150, the high voltage generator 121 starts a pre-heating operation, and when the pre-heating is finished, the high voltage generator 121 outputs a ready signal to the controllers 113 and 150. In addition, the detector 130 also needs to prepare to detect the X-ray, and thus the high voltage generator 121 performs the pre-heating operation and the controllers 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 outputs a ready signal to the controllers 113 and 150.

When the pre-heating operation of the high voltage generator 121 is finished and the detector 130 is ready to detect the X-ray, the controllers 113 and 150 transmit a radiation signal to the high voltage generator 121, the high voltage generator 121 generates and applies the high voltage to the X-ray source 122, and the X-ray source 122 radiates the X-ray.

When the controllers 113 and 150 transmit the radiation signal to the high voltage generator 121, the controllers 113 and 150 may transmit a sound output signal to the output units 111 and 141 so that the output units 111 and 141 output a predetermined sound and the object may recognize the radiation of the X-ray. The output units 111 and 141 may also output a sound representing information related to photographing in addition to the X-ray radiation. In FIG. 1, the output unit 141 is included in the manipulator 140; however, the embodiments are not limited thereto, and the output unit 141 or a portion of the output unit 141 may be located elsewhere. For example, the output unit 141 may be located on a wall of an examination room in which the X-ray photographing of the object is performed.

The controllers 113 and 150 control locations of the X-ray radiator 120 and the detector 130, photographing timing, and photographing conditions, according to photographing conditions set by the user.

In more detail, the controllers 113 and 150 control the high voltage generator 121 and the detector 130 according to the command input via the input units 112 and 142 to control radiation timing of the X-ray, an intensity of the X-ray, and a region radiated by the X-ray. In addition, the control units 113 and 150 adjust the location of the detector 130 according to a predetermined photographing condition, and controls operation timing of the detector 130.

Furthermore, the controllers 113 and 150 generate a medical image of the object by using image data received via the detector 130. In detail, the controllers 113 and 150 may receive the image data from the detector 130, and then, generate the medical image of the object by removing noise from the image data and adjusting a dynamic range and interleaving of the image data.

The output units 111 and 141 may output the medical image generated by the controllers 113 and 150. The output units 111 and 141 may output information that is necessary for the user to manipulate the X-ray apparatus 100, for example, a user interface (UI), user information, or object information. Examples of the output units 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

The workstation 110 shown in FIG. 1 may further include a communicator (not shown) that may be connected to a server 162, a medical apparatus 164, and a portable terminal 166 via a network 15.

The communicator may be connected to the network 15 by wire or wirelessly to communicate with the server 162, the medical apparatus 164, or the portable terminal 166. The communicator may transmit or receive data related to diagnosis of the object via the network 15, and may also transmit or receive medical images captured by the medical apparatus 164, for example, a CT apparatus, an MRI apparatus, or an X-ray apparatus. Moreover, the communicator may receive a medical history or treatment schedule of an object (e.g., a patient) from the server 162 to diagnose a disease of the object. Also, the communicator may perform data communication with the portable terminal 166 such as a mobile phone, a personal digital assistant (PDA), or a laptop computer of a medical doctor or a client, as well as the server 162 or the medical apparatus 164 in a hospital.

The communicator may include one or more elements enabling communication with external apparatuses. For example, the communicator may include a local area communication module, a wired communication module, and a wireless communication module.

The local area communication module refers to a module for performing local area communication with an apparatus located within a predetermined distance. Examples of local area communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module refers to a module for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include a plurality of digital signal processors (DSPs), an ultra-small calculator, and a processing circuit for special purposes (for example, high speed analog/digital (ND) conversion, high speed Fourier transformation, and an array process).

In addition, communication between the workstation 110 and the X-ray apparatus 100 may be performed using a high speed digital interface, such as low voltage differential signalling (LVDS), asynchronous serial communication, such as a universal asynchronous receiver transmitter (UART), a low latency network protocol, such as error synchronous serial communication or a controller area network (CAN), or any of other various communication methods that are well known to one of ordinary skill in the art.

Figure 2:
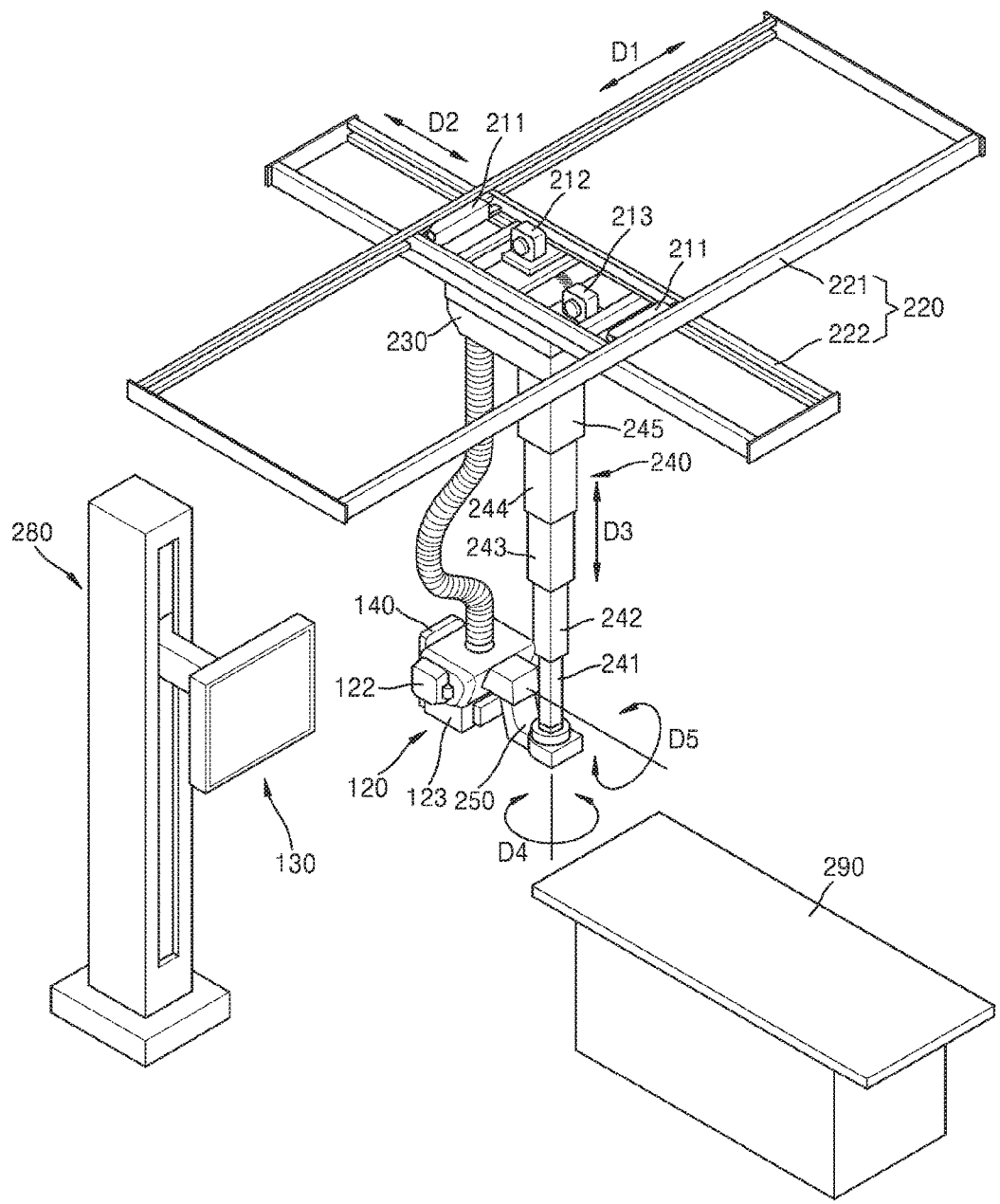
FIG. 2 is a perspective view of a fixed-type X-ray apparatus.

FIG. 2 is a perspective view of a fixed type X-ray apparatus 200. The fixed type X-ray apparatus 200 may be an embodiment of the X-ray apparatus 100 of FIG. 1. Components included in the fixed type X-ray apparatus 200 that are the same as those of the X-ray apparatus 100 of FIG. 1 use the same reference numerals, and repeated descriptions thereof will be omitted.

Referring to FIG. 2, the fixed type X-ray apparatus 200 includes a manipulator 140 providing a user with an interface for manipulating the X-ray apparatus 200, an X-ray radiator 120 radiating an X-ray to an object, a detector 130 detecting an X-ray that has passed through the object, first, second, and third motors 211, 212, and 213 providing a driving power to transport the X-ray radiator 120, a guide rail 220, a moving carriage 230, and a post frame 240. The guide rail 220, the moving carriage 230, and the post frame 240 are formed to transport the X-ray radiator 120 by using the driving power of the first, second, and third motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other at 90°.

The first guide rail 221 is provided on the ceiling of an examination room in which the X-ray apparatus 200 is disposed.

The second guide rail 222 is located under the first guide rail 221, and is mounted to slide along the first guide rail 221. A roller (not shown) that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90°, and may be parallel to the ceiling of the examination room.

The moving carriage 230 is disposed under the second guide rail 222 to move along the second guide rail 222. A roller (not shown) moving along the second guide rail 222 may be provided on the moving carriage 230.

Therefore, the moving carriage 230 may move in the first direction D1 together with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be extendable, and thus, the post frame 240 may have a length that is adjustable in a vertical direction of the examination room while in a state of being fixed to the moving carriage 230.

A third direction D3 is defined as a direction in which the length of the post frame 240 increases or decreases. Therefore, the third direction D3 may be perpendicular to the first direction D1 and the second direction D2.

The detector 130 detects the X-ray that has passed through the object, and may be combined with a table type receptor 290 or a stand type receptor 280.

A rotating joint 250 is disposed between the X-ray radiator 120 and the post frame 240. The rotating joint 250 allows the X-ray radiator 120 to be coupled to the post frame 240, and supports a load applied to the X-ray radiator 120.

The X-ray radiator 120 connected to the rotating joint 250 may rotate on a plane that is perpendicular to the third direction D3. In this case, a rotating direction of the X-ray radiator 120 may be defined as a fourth direction D4.

Also, the X-ray radiator 120 may be configured to be rotatable on a plane perpendicular to the ceiling of the examination room. Therefore, the X-ray radiator 120 may rotate in a fifth direction D5 that is a rotating direction about an axis that is parallel with the first direction D1 or the second direction D2, with respect to the rotating joint 250.

The first, second, and third motors 211, 212, and 213 may be provided to move the X-ray radiator 120 in the first, second, and third directions D1, D2, and D3. The first, second, and third motors 211, 212, and 213 may be electrically driven, and the first, second, and third motors 211, 212, and 213 may respectively include an encoder.

The first, second, and third motors 211, 212, and 213 may be disposed at various locations in consideration of design convenience. For example, the first motor 211, moving the second guide rail 222 in the first direction D1, may be disposed around the first guide rail 221, the second motor 212, moving the moving carriage 230 in the second direction D2, may be disposed around the second guide rail 222, and the third motor 213, increasing or reducing the length of the post frame 240 in the third direction D3, may be disposed in the moving carriage 230. In an example, the first, second, and third motors 211, 212, and 213 may be connected to a driving power transfer unit (not shown) to linearly move the X-ray radiator 120 in the first, second, and third directions D1, D2, and D3. The driving power transfer unit may be a combination of a belt and a pulley, a combination of a chain and a sprocket, or a shaft, which are generally used.

In an example, motors (not shown) may be disposed between the rotating joint 250 and the post frame 240 and between the rotating joint 250 and the X-ray radiator 120 in order to rotate the X-ray radiator 120 in the fourth and fifth directions D4 and D5.

The manipulator 140 may be disposed on a side surface of the X-ray radiator 120.

Although FIG. 2 shows the fixed type X-ray apparatus 200 connected to the ceiling of the examination room, the fixed type X-ray apparatus 200 is merely an example for convenience of comprehension. That is, X-ray apparatuses according to embodiments of the present disclosure may include X-ray apparatuses having various structures that are well known to one of ordinary skill in the art, for example, a C-arm-type X-ray apparatus and an angiography X-ray apparatus, in addition to the fixed type X-ray apparatus 200 of FIG. 2.

Figure 3:
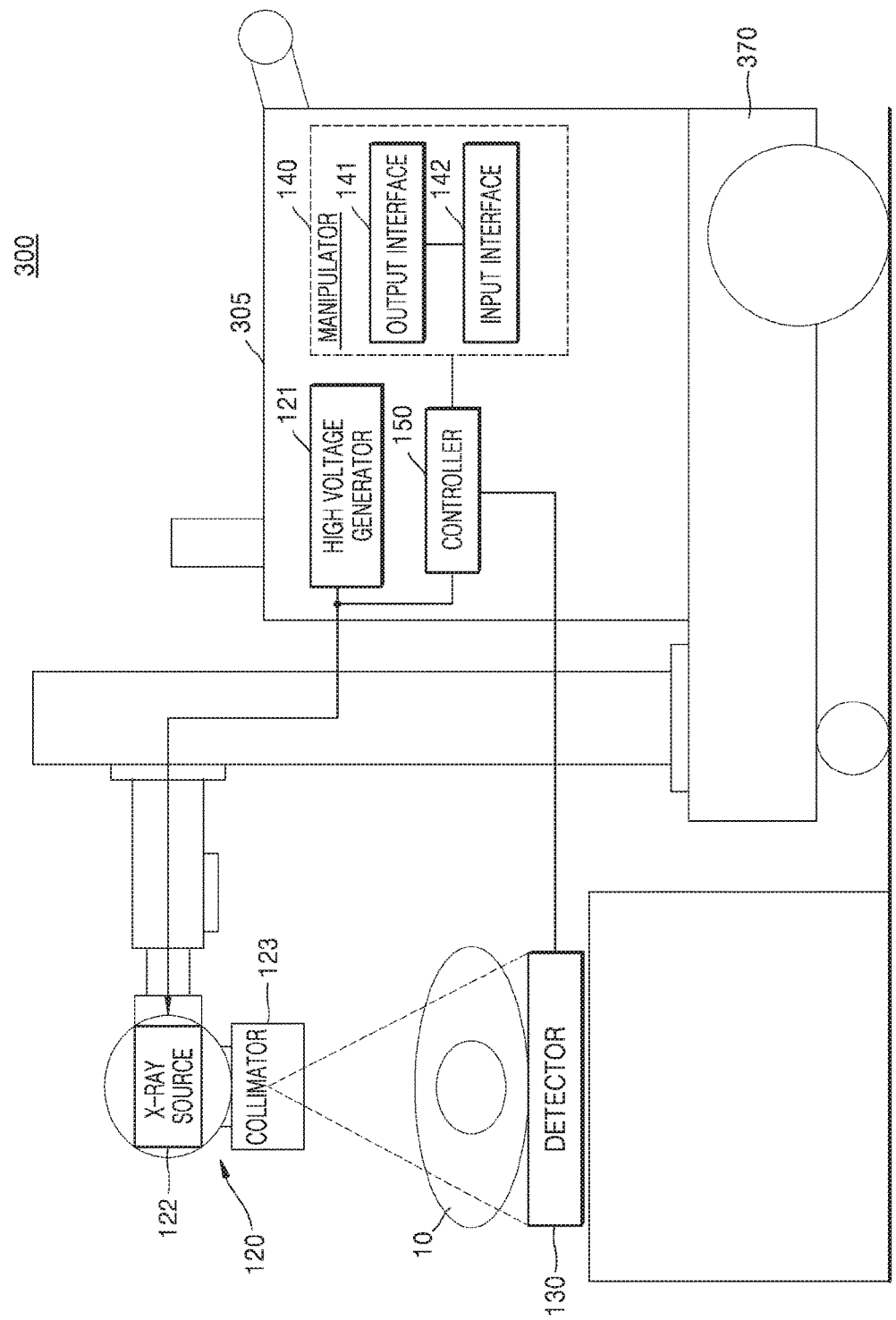
FIG. 3 is a block diagram of a configuration of a mobile X-ray apparatus.

FIG. 3 is a diagram showing a configuration of a mobile X-ray apparatus 300 capable of performing an X-ray photographing operation regardless of a place where the photographing operation is performed. The mobile X-ray apparatus 300 may be an embodiment of the X-ray apparatus 100 of FIG. 1. Components included in the mobile X-ray apparatus 300 that are the same as those of the X-ray apparatus 100 of FIG. 1 use the same reference numerals as those used in FIG. 1, and a repeated description thereof will be omitted.

Referring to FIG. 3, the mobile X-ray apparatus 300 includes a transport unit 370 including a wheel for transporting the mobile X-ray apparatus 300, a main unit 305, an X-ray radiator 120, and a detector 130 detecting an X-ray that is radiated from the X-ray radiator 120 toward an object and transmitted through the object. The main unit 305 includes a manipulator 140 providing a user with an interface for manipulating the mobile X-ray apparatus 300, a high voltage generator 121 generating a high voltage applied to an X-ray source 122, and a controller 150 controlling overall operations of the mobile X-ray apparatus 300. The X-ray radiator 120 includes the X-ray source 122 generating the X-ray, and a collimator 123 guiding a path along which the generated X-ray is emitted from the X-ray source 122 and adjusting an irradiation region radiated by the X-ray.

The detector 130 in FIG. 3 may not be combined with any receptor, and the detector 130 may be a portable detector which can exist anywhere.

In FIG. 3, the manipulator 140 is included in the main unit 305; however, embodiments are not limited thereto. For example, as illustrated in FIG. 2, the manipulator 140 of the mobile X-ray apparatus 300 may be disposed on a side surface of the X-ray radiator 120.

Figure 4:
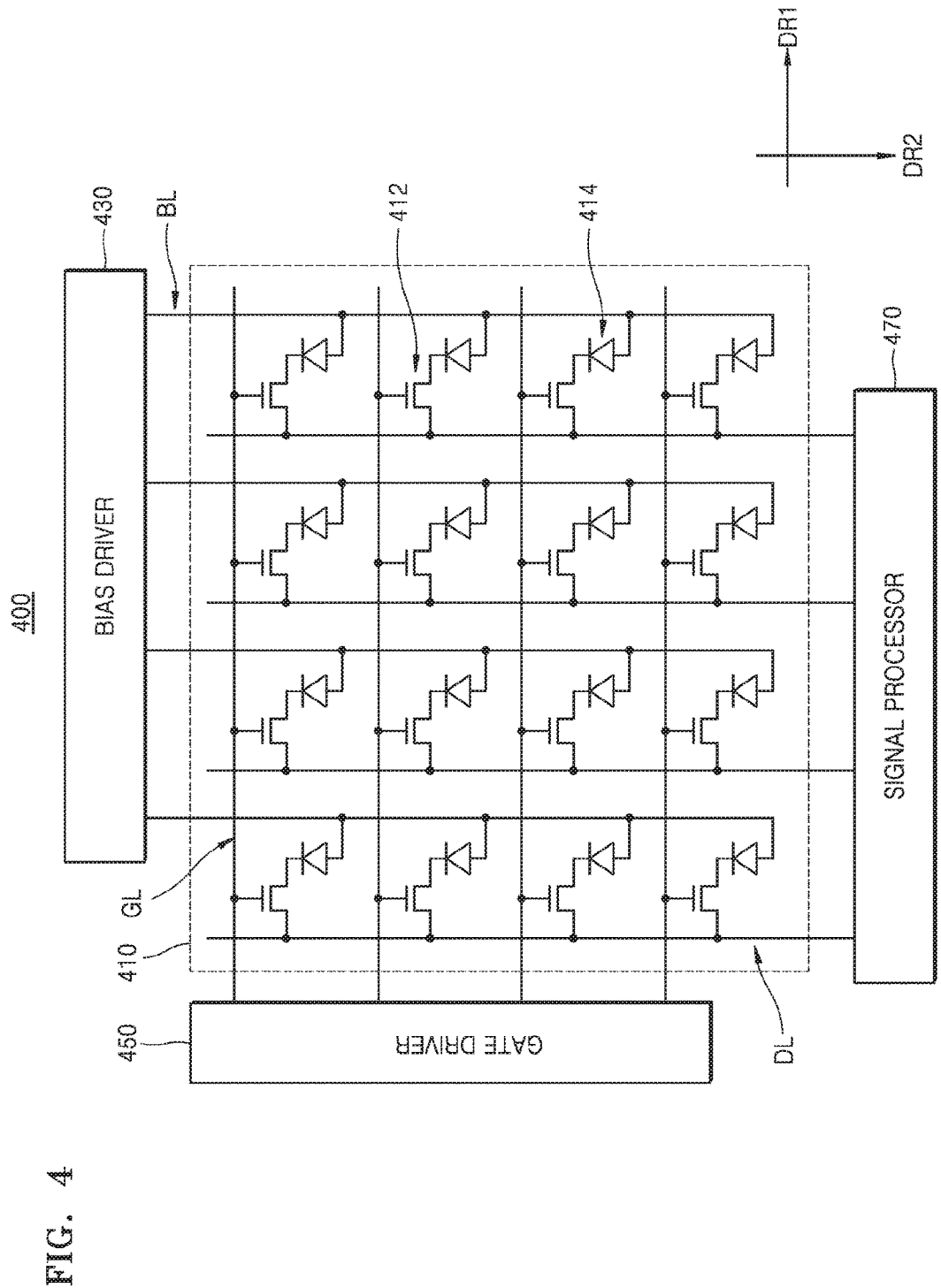
FIG. 4 is a schematic diagram showing a detailed configuration of a detector.

FIG. 4 is a schematic diagram showing a detailed configuration of a detector 400. The detector 400 may be an embodiment of the detector 130 of FIGS. 1-3. The detector 400 may be an indirect type detector.

Referring to FIG. 4, the detector 400 may include a scintillator (not shown), a photodetecting substrate 410, a bias driver 430, a gate driver 450, and a signal processor 470.

The scintillator receives the X-ray radiated from the X-ray source 122 and converts the X-ray into light.

The photodetecting substrate 410 receives the light from the scintillator and converts the light into an electrical signal. The photodetecting substrate 410 may include gate lines GL, data lines DL, TFTs 412, photodiodes 414, and bias lines BL.

The gate lines GL may be formed in the first direction DR1, and the data lines DL may be formed in the second direction DR2 that crosses the first direction DR1. The first direction DR1 and the second direction DR2 may intersect perpendicularly to each other. FIG. 4 shows four gate lines GL and four data lines DL as an example.

The TFTs 412 may be arranged as a matrix in the first and second directions DR1 and DR2. Each of the TFTs 412 may be electrically connected to one of the gate lines GL and one of the data lines DL. A gate of the TFT 412 may be electrically connected to the gate line GL, and a source of the TFT 412 may be electrically connected to the data line DL. In FIG. 4, sixteen TFTs 412 (in a 4×4 arrangement) are shown as an example.

The photodiodes 414 may be arranged as a matrix in the first and second directions DR1 and DR2 to respectively correspond to the TFTs 412. Each of the photodiodes 414 may be electrically connected to one of the TFTs 412. An N-side electrode of each of the photodiodes 414 may be electrically connected to a drain of the TFT 412. FIG. 4 shows sixteen photodiodes 414 (in a 4×4 arrangement) as an example.

The bias lines BL are electrically connected to the photodiodes 414. Each of the bias lines BL may be electrically connected to P-side electrodes of an array of photodiodes 414. For example, the bias lines BL may be formed to be substantially parallel with the second direction DR2 to be electrically connected to the photodiodes 414. On the other hand, the bias lines BL may be formed to be substantially parallel with the first direction DR1 to be electrically connected to the photodiodes 414. FIG. 4 shows four bias lines BL formed along the second direction DR2 as an example.

The bias driver 430 is electrically connected to the bias lines BL to apply a driving voltage to the bias lines BL. The bias driver 430 may selectively apply a reverse bias voltage or a forward bias voltage to the photodiodes 414. A reference voltage may be applied to the N-side electrodes of the photodiodes 414. The reference voltage may be applied via the signal processor 470. The bias driver 430 may apply a voltage that is less than the reference voltage to the P-side electrodes of the photodiodes 414 to apply a reverse bias voltage to the photodiodes 414. On the other hand, the bias driver 430 may apply a voltage that is greater than the reference voltage to the P-side electrodes of the photodiodes 414 to apply a forward bias voltage to the photodiodes 414.

The gate driver 450 is electrically connected to the gate lines GL and thus may apply gate signals to the gate lines GL. For example, when the gate signals are applied to the gate lines GL, the TFTs 412 may be turned on by the gate signals. On the other hand, when the gate signals are not applied to the gate lines GL, the TFTs 412 may be turned off.

The signal processor 470 is electrically connected to the data lines DL. When the light received by the photodetecting substrate 410 is converted into the electrical signal, the electrical signal may be read out by the signal processor 470 via the data lines DL.

An operation of the detector 400 will now be described. During the operation of the detector 400, the bias driver 430 may apply the reverse bias voltage to the photodiodes 414.

While the TFTs 412 are turned off, each of the photodiodes 414 may receive the light from the scintillator and generate electron-hole pairs to accumulate electric charges. The amount of electric charge accumulated in each of the photodiodes 414 may correspond to the intensity of the received X-ray.

Then, the gate driver 450 may sequentially apply the gate signals to the gate lines GL along the second direction DR2. When a gate signal is applied to a gate line GL and thus TFTs 412 connected to the gate line GL are turned on, photocurrents may flow into the signal processor 470 via the data lines DL due to the electric charges accumulated in the photodiodes 414 connected to the turned-on TFTs 412.

The signal processor 470 may convert the received photocurrents into image data. The signal processor 470 may output the image data to the outside. The image data may be in the form of an analog signal or a digital signal corresponding to the photocurrents.

Although not shown in FIG. 4, if the detector 400 shown in FIG. 4 is a wireless detector, the detector 400 may further include a battery unit and a wireless communication interface unit.

Figure 5:
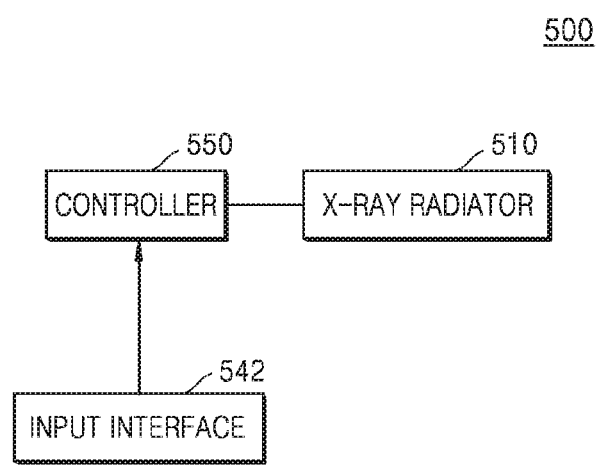
FIG. 5 is a block diagram of a configuration of an X-ray apparatus according to an embodiment.

FIG. 5 illustrates an X-ray apparatus 500 according to an embodiment.

Referring to FIG. 5, the X-ray apparatus 500 according to the present embodiment may include an X-ray radiator 510, an input unit 542, and a controller 550. The X-ray radiator 510 may include an X-ray source 511 and a collimator 512.

The input interface 542 may receive a user input for setting an X-ray imaging area with respect to an object. The input interface 542 may receive a user input for setting an X-ray imaging area in various ways. In detail, an output interface (not shown) may display a photographic image obtained by photographing the object, and the input interface 543 may receive a user input for setting an X-ray imaging area in the photographic image. For example, the input interface 542 may receive a user input for selecting a start point and an end point of the X-ray imaging area, but embodiments are not limited thereto.

The controller 550 may divide an X-ray imaging area set according to a user input received by the input interface 542 into a plurality of partial X-ray imaging regions. Furthermore, the controller 550 may determine an order of imaging operations performed with respect to the plurality of partial X-ray imaging regions based on a size information of the object represented on the plurality of partial X-ray imaging regions. The information of the object may include information about portions of the object respectively represented on the plurality of partial X-ray imaging regions, such as information about an area of the object and information about a width of the object represented thereon.

According to an embodiment, the controller 550 may determine the order of imaging operations based on an area of the object represented on each of the plurality of partial X-ray imaging regions. The controller 550 may determine the order of the imaging operations as being an order from a partial X-ray imaging region where a portion of the object having a large area is represented on a partial X-ray imaging region where a portion of the object having a small area is represented.

Alternatively, the controller 550 may determine the order of imaging operations as being an order from a partial X-ray imaging region where a portion of the object having a large width is represented on a partial X-ray imaging region where a portion of the object having a small width is represented. According to an embodiment, information of the object may be a width of the object in a direction perpendicular to a direction in which imaging operations are performed with respect to the plurality of partial X-ray imaging regions.

The X-ray radiator 510 may radiate X-rays onto a plurality of partial X-ray imaging regions according to the order determined by the controller 550 in order to perform partial imaging operations on the object.

A detector (not shown) may detect X-rays that are radiated by the X-ray radiator 510 and transmitted through the object.

The components of the X-ray apparatus 500 described with reference to FIG. 5 may be the same as the components of the X-ray apparatus 100 described with reference to FIG. 1. For example, the X-ray radiator 510 and the input interface 542 described with reference to FIG. 5 may respectively correspond to the X-ray radiator 120 and the input interface 142 described with reference to FIG. 1. Thus, other descriptions of the components that are already provided with respect to FIG. 1 will be omitted below.

Furthermore, the X-ray apparatus 500 may be controlled by the workstation (110 of FIG. 1).

The configuration and functions of the X-ray apparatus 500 will now be described in more detail with reference to FIGS. 6 through 9.

Figure 6:
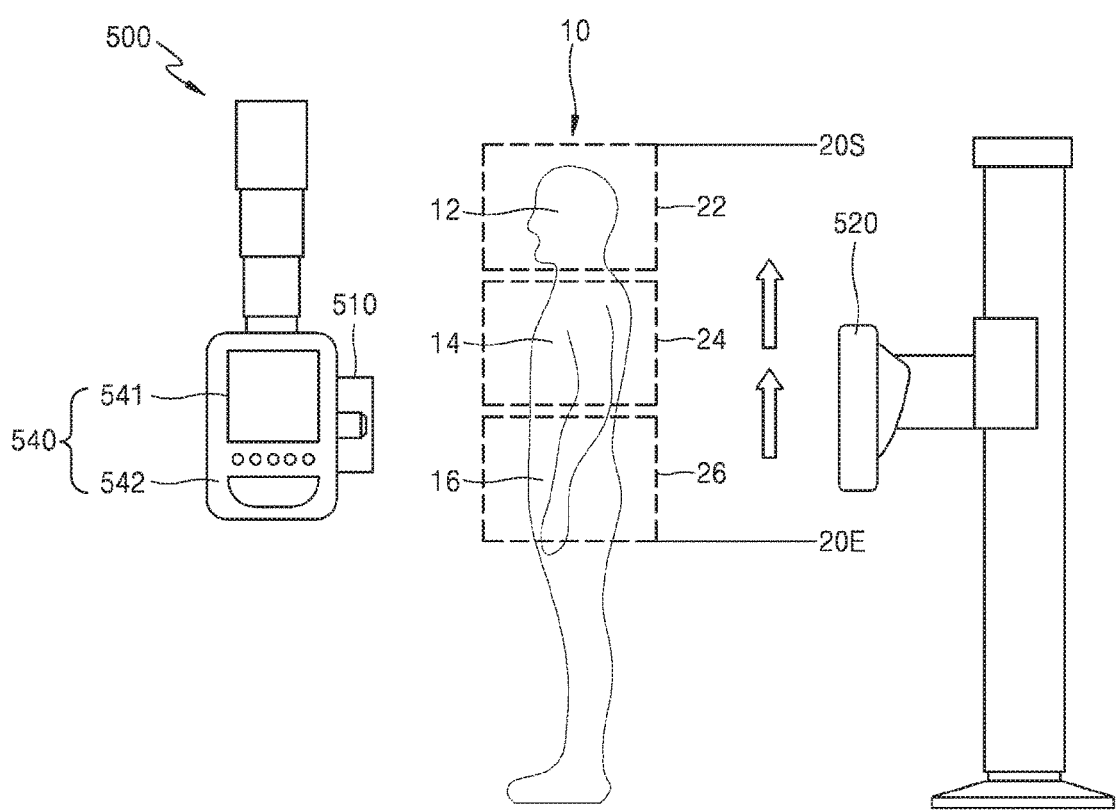
FIG. 6 illustrates an X-ray apparatus and a method of performing X-ray imaging according to embodiments.

FIG. 6 illustrates the X-ray apparatus 500 and a method of performing X-ray imaging via the X-ray apparatus 500.

Referring to FIG. 6, the X-ray apparatus 500 may further include a detector 520. Furthermore, the X-ray apparatus 500 may further include a manipulator 540 consisting of an output interface 541 and an input interface 542. The input interface 542 may receive a user input for setting an X-ray imaging area with respect to an object 10. The input interface 542 may receive a user input for setting a start point 20S and an end point 20E where X-ray imaging of the object 10 respectively starts and ends. For example, the input interface 542 may receive a user input for setting the X-ray imaging area to be an area ranging from the skull to the abdomen. The X-ray imaging area (i.e., an area from the start point 20S to the end point 20E) set by the input interface 542 with respect to the object 10 may be displayed on the output interface 541.

The controller (550 of FIG. 5) may divide the X-ray imaging area (the area from the start point 20S to the end point 20E) with respect to the object 10 into a plurality of partial X-ray imaging regions 22, 24, and 26. The plurality of partial X-ray imaging regions 22, 24, and 26 may each have the same size but are not limited thereto. According to an embodiment, the plurality of partial X-ray imaging regions 22, 24, and 26 may include first through third partial X-ray imaging regions 22, 24, and 26. However, embodiments are not limited thereto, and the plurality of partial X-ray imaging regions may include two or four or more partial imaging regions. Although FIG. 6 shows that the plurality of partial X-ray imaging regions 22, 24, and 26 are separated from one another for convenience of explanation, they may each have overlapping portions therebetween including the same portions of the object 10.

According to an embodiment, the plurality of first through third partial X-ray imaging regions 22, 24, and 26 may respectively include a skull 12, a thorax 14, and an abdomen 16 of the object 10.

The controller 550 may determine the order of imaging operations with respect to the plurality of partial X-ray imaging regions 22, 24, and 26.

According to an embodiment, the controller 550 may determine the order of imaging operations according to the order from a partial X-ray imaging region where a portion of the object 10 having a large area is represented on a partial X-ray imaging region where a portion of the object 10 having a small area is represented. The controller 550 may determine the order of imaging operations so that the imaging operations are performed in the order from a partial X-ray imaging region corresponding to a portion of the object 10 having a large area to a partial X-ray imaging region corresponding to a portion of the object 10 having a small area.

According to an embodiment, the controller 550 may determine the order of imaging operations according to a descending order based on widths of portions of the object 10 respectively represented on the plurality of first through third partial X-ray imaging regions 22, 24, and 26. In other words, the controller 550 may determine the order of imaging operations so that the imaging operations are performed in the order from a partial X-ray imaging region where a portion of the object 10 having a large width is represented on a partial X-ray imaging region where a portion of the object 10 having a small width is represented. For example, the controller 550 may determine the order of imaging operations so that the imaging operations are performed in an order from the third partial X-ray imaging region 26 including the abdomen 16 of the object 10 to the second partial X-ray imaging region 24 including the thorax 14 to the first partial X-ray imaging region 22 including the skull 12. However, embodiments are not limited thereto, and if the second partial X-ray imaging region 24 onto which the thorax 14 of the object is represented has a greatest width, the controller 550 may determine the order of imaging operations so that the imaging operations are performed on the second partial X-ray imaging region 24 earlier than on the third partial X-ray imaging region 26.

The X-ray radiator 510 may radiate X-rays on the plurality of partial X-ray imaging regions 22, 24, and 26 according to the order determined by the controller 550. According to an embodiment, the X-ray radiator 510 may radiate X-rays as it moves from the third partial X-ray imaging region 26 including the abdomen 16 of the object 10 toward the first partial X-ray imaging region 22 including the skull 12 of the object 10.

According to an embodiment, the X-ray apparatus 500 is configured to determine the order of imaging according to the order from a portion of the object 10 having a large area or width to a portion thereof having a small area or width, thereby preventing generation of after-images in a preceding imaging region due to partial imaging, In detail, in partial X-ray imaging that is performed within a short time, if X-ray imaging is performed in the order from a portion of the object 10 having a small area or width to a portion thereof having a large area or width, an excessive amount of X-rays may be incident on the detector 520 during the X-ray imaging with respect to a partial imaging region corresponding to a portion of the object 10 having a small area or width. Thus, a ghost image may appear during subsequent X-ray imaging of a portion of the object 10 having a large area or width. According to an embodiment, the X-ray apparatus 500 is configured to divide an X-ray imaging area set with respect to the object 10 into a plurality of partial X-ray imaging regions and determine the order of partial X-ray imaging operations based on size information of the object 10 represented on each of the plurality of partial X-ray imaging regions. Thus, even when an after-image or ghost image is produced due to an excessive amount of X-rays being incident on the detector 520 during large-area X-ray imaging, the after-image or ghost image may appear in only a background region for small-area X-ray imaging, which may minimize an adverse effect on the quality of the small-area X-ray imaging Thus, the quality of an X-ray image of the object 10 may be improved.

Figure 7A:
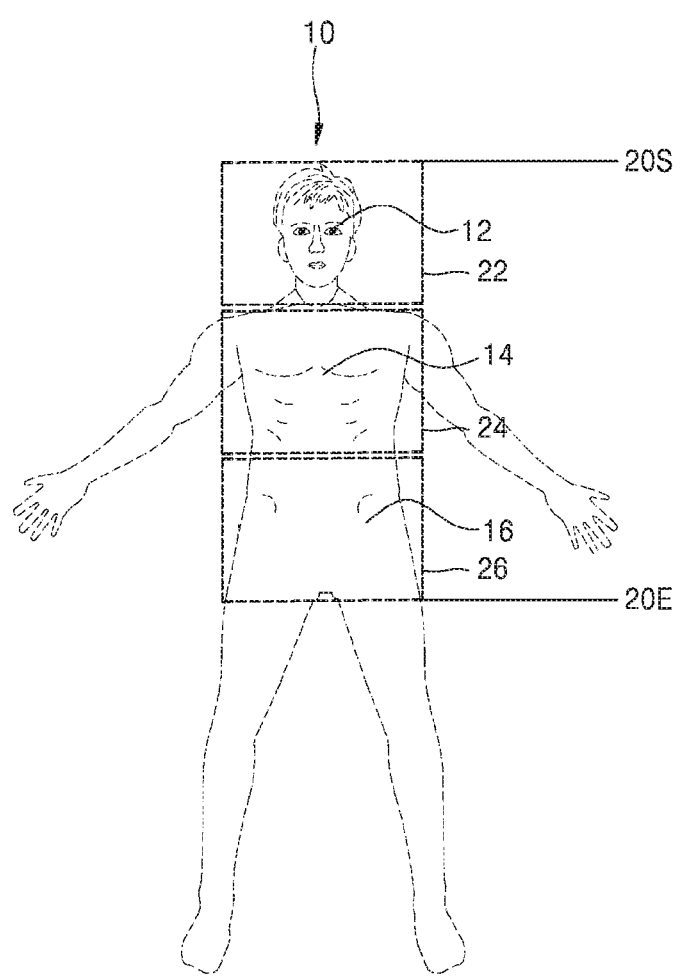
FIG. 7A illustrates a relation between partial X-ray imaging regions and portions of an object respectively projected thereon.
Figure 7B:
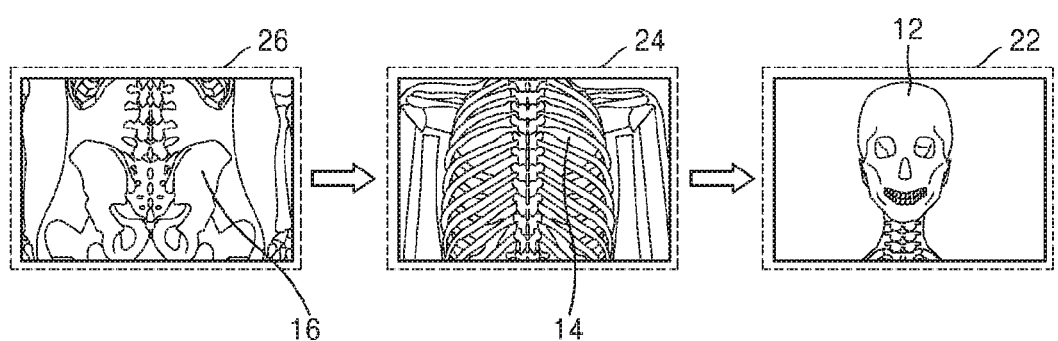
FIGS. 7B and 7C include diagrams for explaining an order of imaging operations determined by an X-ray apparatus.

FIG. 7A illustrates the relation between a plurality of partial X-ray imaging regions, i.e., first through third X-ray imaging regions 22, 24, and 26 and portions of an object 10 respectively represented thereon, and FIG. 7B are diagrams for explaining the order of imaging operations with respect to the first through third partial X-ray imaging regions 22, 24, and 26 and being determined by the X-ray apparatus 500.

Referring to FIG. 7A, the controller (550 described with reference to FIGS. 5 and 6) may acquire size information about areas of portions of the object 10 respectively represented on the plurality of partial X-ray imaging regions 22, 24, and 26.

The detector (520 described with reference to FIGS. 5 and 6) may detect X-rays irradiated on the first through third partial X-ray imaging regions 22, 24, and 26.

FIG. 7B may be an example in which the controller 550 may determine that a portion of the object 10 being represented on the third partial X-ray imaging region 26 has a greatest area, a portion of the object 10 being represented on the second partial X-ray imaging region 24 has a second greatest area, and a portion of the object 10 being represented on the first partial X-ray imaging region 22 has a smallest area.

Referring to FIG. 7B, the controller 550 may determine the order of imaging operations so that the imaging operations are performed in the order from the third partial X-ray imaging region 26 including an abdomen 16 of the object 10 to the second partial X-ray imaging region 24 including a thorax 14 to the first partial X-ray imaging region 22 including a skull 12.

Figure 7C:
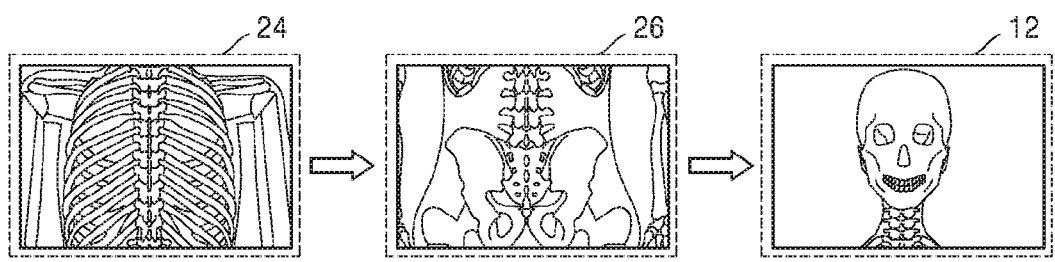

Referring to FIG. 7C, the controller 550 may determine the order of imaging operations so that the imaging operations are performed in the order from the second partial X-ray imaging region 24 including the thorax 14 of the object 10 to the third partial X-ray imaging region 26 including the abdomen 16 to the first partial X-ray imaging region 22 including the skull 12. In this case, the thorax 14 of the object 10 represented on the second partial X-ray imaging region 24 may have a greater area than that of the abdomen 16 of the object 10 represented on the third partial X-ray imaging region 26.

Figure 8:
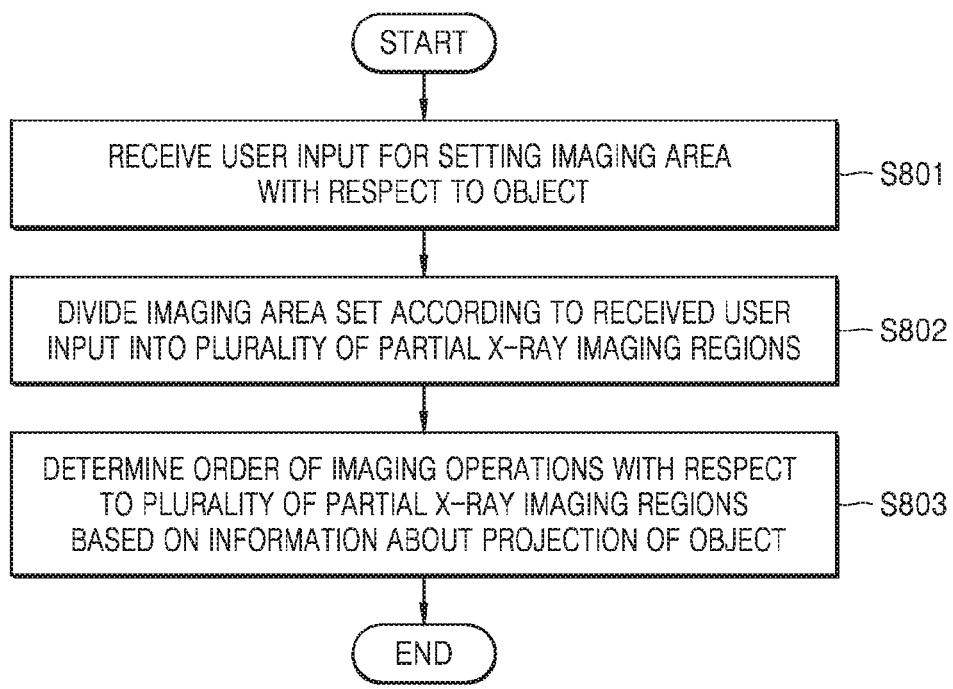
FIG. 8 is a flowchart of a method, performed by an X-ray apparatus, of performing partial imaging, according to an embodiment.

FIG. 8 is a flowchart of a method, performed by an X-ray apparatus, of performing partial imaging, according to an embodiment.

The X-ray apparatus receives a user input for setting an X-ray imaging area with respect to an object (operation S801).

The X-ray apparatus divides an imaging area set according to a user input into a plurality of partial X-ray imaging regions (operation S802). According to an embodiment, the X-ray apparatus may divide an X-ray imaging area with respect to the object 10 into three (3) partial X-ray imaging regions including the first through third partial X-ray imaging regions (22, 24, and 26 described with reference to FIGS. 7A and 7B. However, the number of the plurality of partial X-ray imaging regions is not limited to three (3).

The X-ray apparatus determines the order of imaging operations with respect to the plurality of partial X-ray imaging regions (operation S803). According to an embodiment, the X-ray apparatus may determine the order of imaging operations based on a size information of the object represented on each of the plurality of partial X-ray imaging regions. The size information of the object may include information of object represented on each of the plurality of partial X-ray imaging regions, such as information about an area of the object represented thereon and information about a width of the object represented thereon.

According to an embodiment, the X-ray apparatus may determine the order of imaging operations in the order from a partial imaging region where a portion of the object having a large area is represented on a partial imaging region where a portion of the object having a small area is represented.

The method of FIG. 8 may be performed by the X-ray apparatus 500 of FIG. 5.

Figure 9:
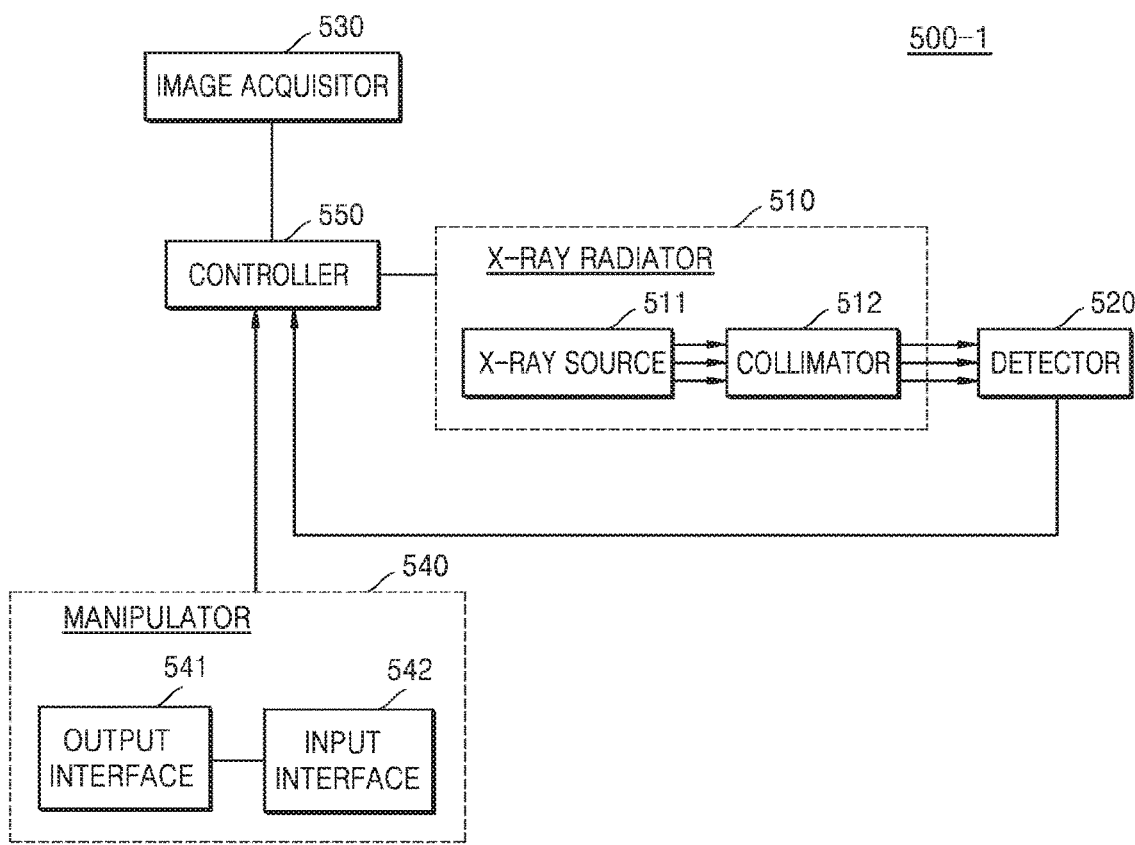
FIG. 9 is a block diagram of a configuration of an X-ray apparatus according to an embodiment.

FIG. 9 is a block diagram of a configuration of an X-ray apparatus 500-1 according to an embodiment. The X-ray apparatus 500-1 may further include an image acquisitioner 530. Because components of the X-ray apparatus 500-1 other than the image acquisitioner 530 respectively correspond to their counterparts of the X-ray apparatus 500 described with reference to FIG. 5, descriptions already provided with respect to FIG. 5 will be omitted below.

Referring to FIG. 9, the X-ray apparatus 500-1 according to the present embodiment may further include the image acquisitioner 530. The image acquisitioner 530 may acquire a photographic image of the object (10 of FIG. 6) by photographing the object 10. The photographic image is distinguished from an X-ray image obtained by taking an X-ray of the object 10. The image acquisitioner 530 may be implemented using a camera that is a general image acquisition device. Furthermore, the controller 550 may acquire, based on the photographic image, a size information of the object 10 represented on a plurality of partial X-ray imaging regions, e. g., information about areas of portions of the object 10 respectively represented on the plurality of partial X-ray imaging regions. The image acquisitioner 530 may provide the acquired photographic image to a controller 550. The photographic image may be displayed on an output interface 541.

The controller 550 may determine the order of imaging operations with respect to the plurality of partial X-ray imaging regions based on the photographic image provided by the image acquisitioner 530. According to an embodiment, the controller 550 may determine, based on the photographic image provided by the image acquisitioner 530, the order of imaging operations according to the order from a partial X-ray imaging region where a portion of the object 10 having a greatest area is represented on a partial X-ray imaging region where a portion of the object 10 having a smallest area is represented.

Figure 10:
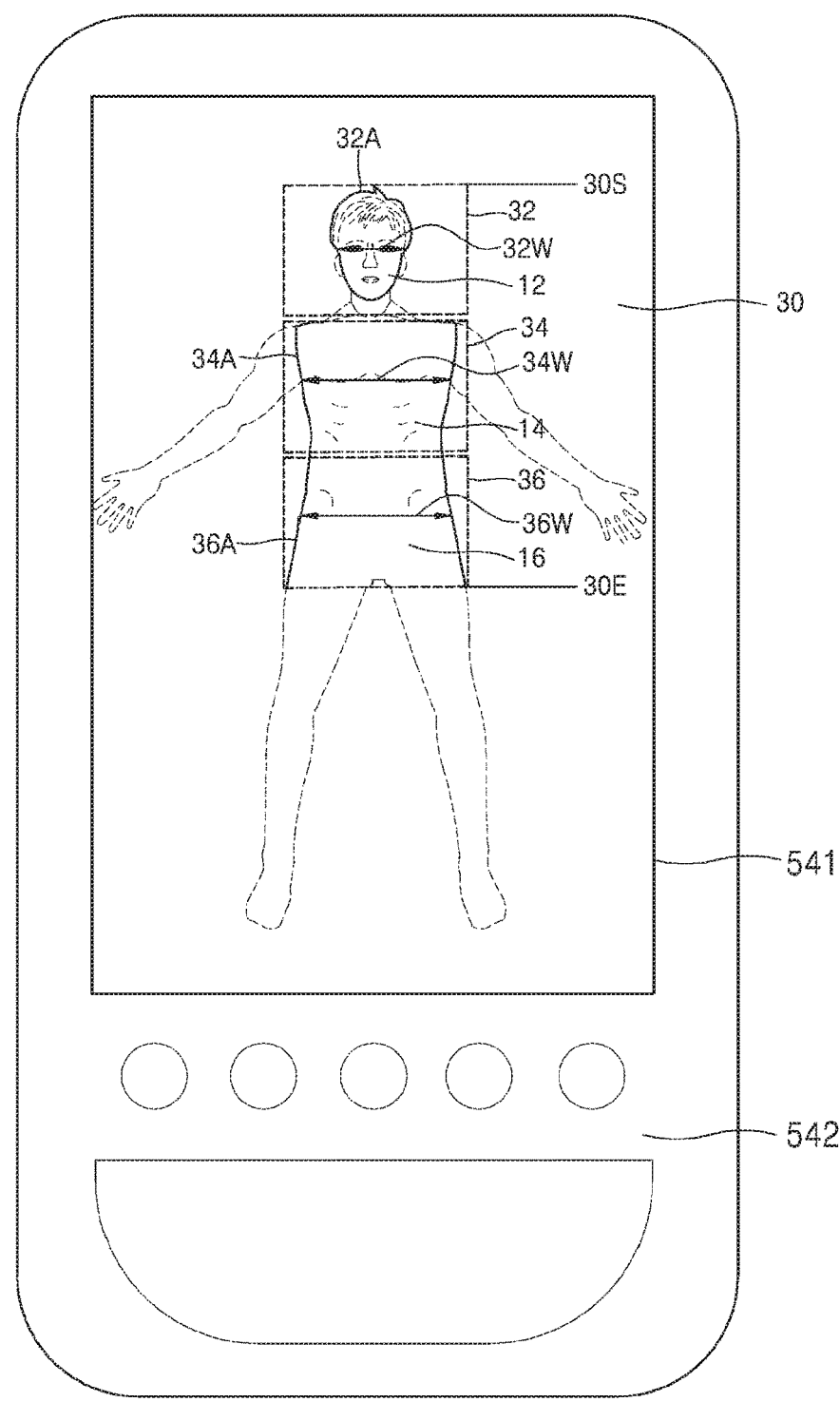
FIG. 10 illustrates a photographic image of an object obtained by an X-ray apparatus according to an embodiment.

FIG. 10 illustrates a photographic image 30 of an object 10 obtained by the X-ray apparatus (500-1 of FIG. 9) according to an embodiment. In detail, the photographic image 30 may be obtained by photographing the object 10 via the image acquisitioner 530. The photographic image 30 may be displayed on the output interface 541.

Referring to FIG. 10, the image acquisitioner 530 may acquire the photographic image 30 by photographing the object 10. According to an embodiment, the controller 550 may acquire, from the photographic image 30, a size information of the object 10 represented on a plurality of partial X-ray imaging regions, i.e., first through third partial X-ray imaging regions 32, 34, and 36 indicated on the photographic image 30.

According to an embodiment, the controller 550 may acquire information about a width 32W of a skull 12 of the object 10 included in the first partial X-ray imaging region 32, a width 34W of a thorax 14 of the object 10 included in the second partial X-ray imaging region 34, and a width 36W of an abdomen 16 of the object 10 included in the third partial X-ray imaging region 36.

According to an embodiment, the controller 550 may acquire information about an area 32A of a portion including the skull 12 of the object 10 included in the first partial X-ray imaging region 32, an area 34A of a portion including the thorax 14 of the object 10 included in the second partial X-ray imaging region 34, and an area 36A of a portion including the abdomen 16 of the object 10 included in the third partial X-ray imaging region 36.

Figure 11:
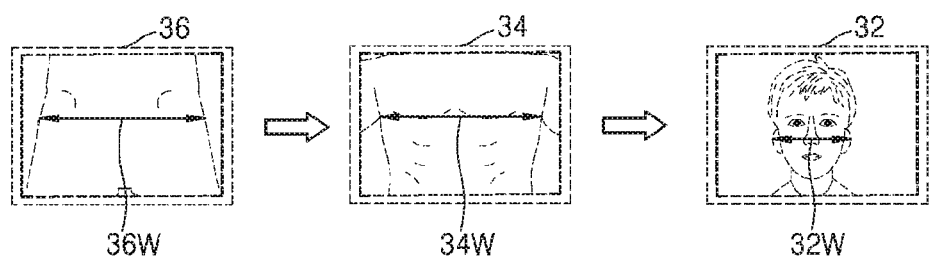
FIG. 11 is a diagram for explaining a method, performed by an X-ray apparatus, of performing partial imaging on an object according to an embodiment.

FIG. 11 is a diagram for explaining a method, performed by the X-ray apparatus (500-1 of FIG. 9), of performing partial imaging on an object 10 according to an embodiment.

Referring to FIG. 11, the X-ray apparatus 500-1 may acquire the photographic image (30 of FIG. 10) of the object 10 and determine the order of imaging operations with respect to the plurality of partial X-ray imaging regions 32, 34, and 36 based on size information of the object 10 represented on the plurality of partial X-ray imaging regions 32, 34, and 36 acquired from the photographic image 30.

According to an embodiment, the image acquisitioner 530 may obtain the photographic image 30 by photographing the object 10 and acquire information about widths of the object 10.

The controller 550 may divide an X-ray imaging area set with respect to the object 10 into the plurality of partial X-ray imaging regions 32, 34, and 36 and determine the order of imaging operations with respect to the plurality of partial X-ray imaging regions 32, 34, and 36, based on information about widths of the object 10 acquired by the image acquisitioner 530. According to an embodiment, the controller 550 may acquire, via the image acquisitioner 530, data with respect to the width 32W of the skull 12 of the object 10 included in the first partial X-ray imaging region 32, the width 34W of the thorax 14 included in the second partial X-ray imaging region 34, and the width 36W of the abdomen 16 included in the third partial X-ray imaging region 36, and determine, based on the acquired data, the order of imaging operations according to the order from a partial X-ray imaging region corresponding to a portion of the object 10 having a greatest width to a partial X-ray imaging region corresponding to a portion of the object 10 having a smallest width. The controller 550 may determine the order of imaging operations so that the imaging operations are performed in the order from the third partial X-ray imaging region 36 including the abdomen 16 to the second partial X-ray imaging region 34 including the thorax 14 to the first partial X-ray imaging region 32 including the skull 12. However, embodiments are not limited thereto, and if a width of the thorax 14 of the object 10 is greater than that of the abdomen 16, the controller 550 may control imaging operations to be performed on the second partial X-ray imaging region 34 earlier than on the third partial X-ray imaging region 36.

Figure 12:
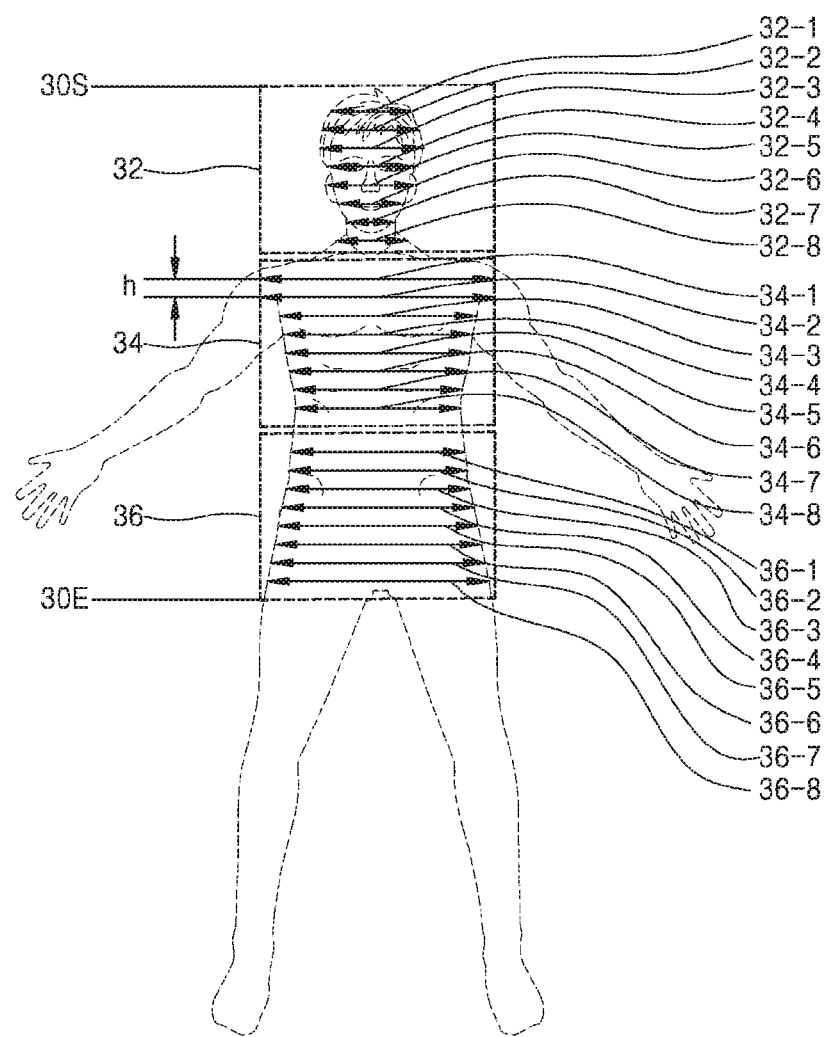
FIG. 12 is a diagram for explaining a method, performed by an X-ray apparatus, of performing partial imaging on an object, according to an embodiment.

FIG. 12 is a diagram for explaining a method, performed by the X-ray apparatus 500-1, of performing partial imaging on an object according to an embodiment.

Referring to FIG. 12, the X-ray apparatus 500-1 may measure widths of portions of the object 10 respectively represented on a plurality of partial X-ray imaging regions 32, 34, and 36 at sampling intervals that are uniformly spaced in a direction perpendicular to the object 10, acquire representative values of the measured widths of the portions of the object 10, and determine the order of imaging operations with respect to the plurality of partial X-ray imaging regions 32, 34, and 36 based on the acquired representative values.

According to an embodiment, the manipulator (540 of FIG. 9) may receive a user input for setting a start point 30S and an end point 30E of an X-ray imaging area with respect to the object 10. The controller 550 may divide the X-ray imaging area set based on the user input into a plurality of partial X-ray imaging regions 32, 34, and 36, i.e., first through third partial X-ray imaging regions 32, 34, and 36, and measure widths of a portion of the object 10 represented on each of the plurality of partial X-ray imaging regions 32, 34, and 36 at predetermined sampling intervals h. According to an embodiment, the controller 550 may divide a portion connecting a skull to a c-spine and a shoulder and represented on the first partial X-ray imaging region 32 by the predetermined sampling intervals h in a direction perpendicular to the object 10 and acquire a plurality of first sample values 32-1 through 32-8. Similarly, the controller 550 may divide a portion including a thorax of the object 10 and represented on the second partial X-ray imaging region 34 by the predetermined sampling intervals h in a direction perpendicular to the object 10 and acquire a plurality of second sample values 34-1 through 34-8. Furthermore, the controller 550 may divide a portion including an abdomen and a pelvis and represented on the third partial X-ray imaging region 36 by the predetermined sampling intervals h and acquire a plurality of third sample values 36-1 through 36-8. While FIG. 12 shows that the number of sample values is eight (8) for convenience of explanation, the number of sample values is not limited to 8.

According to an embodiment, the controller 550 may receive image data and the photographic image (30 of FIG. 10) obtained by photographing the object 10 via the image acquisitioner 530 and acquire the first sample values 32-1 through 32-8, the second sample values 34-1 through 34-8, and the third sample values 36-1 through 36-8.

The controller 550 may acquire representative values of widths of the object 10 represented on the plurality of partial X-ray imaging regions 32, 34, and 36 based on the acquired first through third sample values 32-1 through 32-8, 34-1 through 34-8, and 36-1 through 36-8. A representative value may be at least one of an average value, a minimum value, a maximum value, and a median value of a plurality of sample values. According to an embodiment, the controller 550 may calculate an average value of widths of the object 10 represented on the first partial X-ray imaging region 32 by adding together the plurality of first sampling values 32-1 through 32-8 and then dividing the resulting sum by the number of samples. In the same manner, the controller 550 may calculate an average value of widths of the object 10 represented on the second partial X-ray imaging region 34 by adding together the plurality of second sampling values 34-1 through 34-8 and then dividing the resulting sum by the number of samples. Furthermore, the controller 550 may calculate an average value of widths of the object 10 represented on the third partial X-ray imaging region 36 by adding together the plurality of third sampling values 36-1 through 36-8 and then dividing the resulting sum by the number of samples.

The controller 550 may determine the order of imaging operations with respect to the first through third partial X-ray imaging regions 32, 34, and 36 based on corresponding average values of widths of the object 10 represented thereon. According to an embodiment, when a third average value that is an average value of widths of the object 10 represented on the third partial X-ray imaging region 36 is greater than a second average value that is an average value of widths of the object 10 represented on the second partial X-ray imaging region 34, the controller 550 may determine the order of imaging operations according to the order from the third partial X-ray imaging region 36 to the first partial X-ray imaging region 32. According to an embodiment, when a second average value that is an average value of widths in a transverse direction of the object 10 represented on the second partial X-ray imaging region 34 is greater than a third average value that is an average value of widths of the object 10 represented on the third partial X-ray imaging region 34, the controller 550 may determine the order of imaging operations so that the imaging operations may be performed in the order from the second partial X-ray imaging region 34 to the third partial X-ray imaging region 36 to the first partial X-ray imaging region 32.

The controller 550 may determine the order of imaging operations with respect to the plurality of partial X-ray imaging regions 32, 34, and 36 based on one of representative values, i.e., a minimum value, a median value, and a maximum value, of widths of the object 10 represented on each of the plurality of partial X-ray imaging regions 32, 34, and 36. For example, if a median value of the plurality of third sample values 36-1 through 36-8 is greater than a median value of the plurality of second sample values 34-1 through 34-8, the controller 550 may determine the order of imaging operations so that the imaging operations are performed on the third partial X-ray imaging region 36 earlier than on the second partial X-ray imaging region 34.

Figure 13:
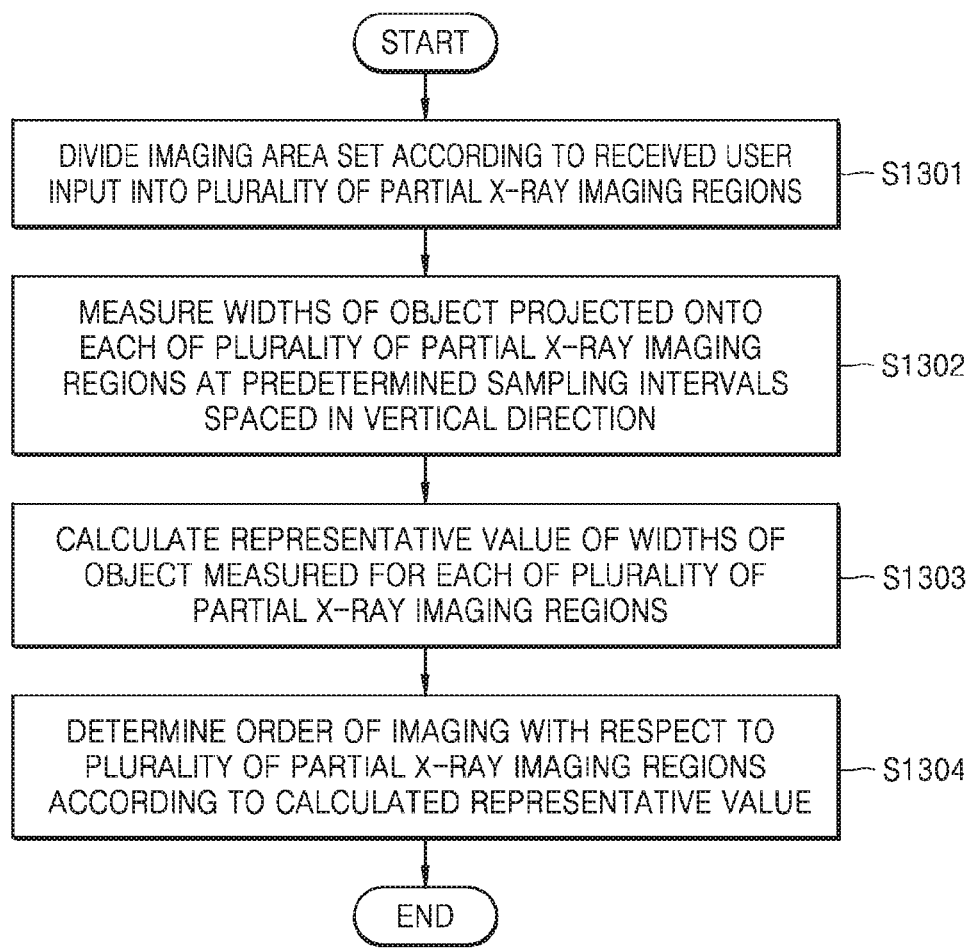
FIG. 13 is a flowchart of a method, performed by an X-ray apparatus, of performing partial imaging on an object, according to an embodiment.

FIG. 13 is a flowchart of a method, performed by the X-ray apparatus 500-1, of performing partial imaging on the object 10 according to an embodiment.

The X-ray apparatus 500-1 divides an imaging area set based on a received user input into a plurality of partial X-ray imaging regions (operation S1301). In detail, the input interface (542 of FIG. 9) may receive a user input for setting an X-ray imaging area with respect to the object 10. The controller 550 may divide the X-ray imaging area set based on the user input into a plurality of partial X-ray imaging regions.

The X-ray apparatus 500-1 may measure widths of a portion of the object 10 represented on each of the plurality of partial X-ray imaging regions at predetermined sampling intervals (operation S1302). In detail, the controller 550 may acquire a plurality of sample values of widths by measuring widths of a portion of the object 10 represented on each of the plurality of partial X-ray imaging regions at predetermined sampling intervals that are spaced in a direction perpendicular to the direction of width of the object 10.

The X-ray apparatus 500-1 calculates representative values of widths of portions of the object 10 measured for the plurality of partial X-ray imaging regions (operation S1303). A representative value may be at least one of an average value, a minimum value, a median value, and a maximum value. According to an embodiment, the controller 550 may calculate a representative value such as an average value based on sample values of a width of the object 10 measured for each of the plurality of partial X-ray imaging regions.

The X-ray apparatus 500-1 determines the order of imaging operations with respect to the plurality of partial X-ray imaging regions based on the calculated representative values (operation S1304). According to an embodiment, the controller 550 may determine the order of imaging operations so that the imaging operations are performed in the order from a partial X-ray imaging region for which a large representative value is calculated to a partial X-ray imaging region for which a small representative value is calculated.

The method of FIG. 13 may be performed by the X-ray apparatus 500-1 of FIG. 9.

Figure 14:
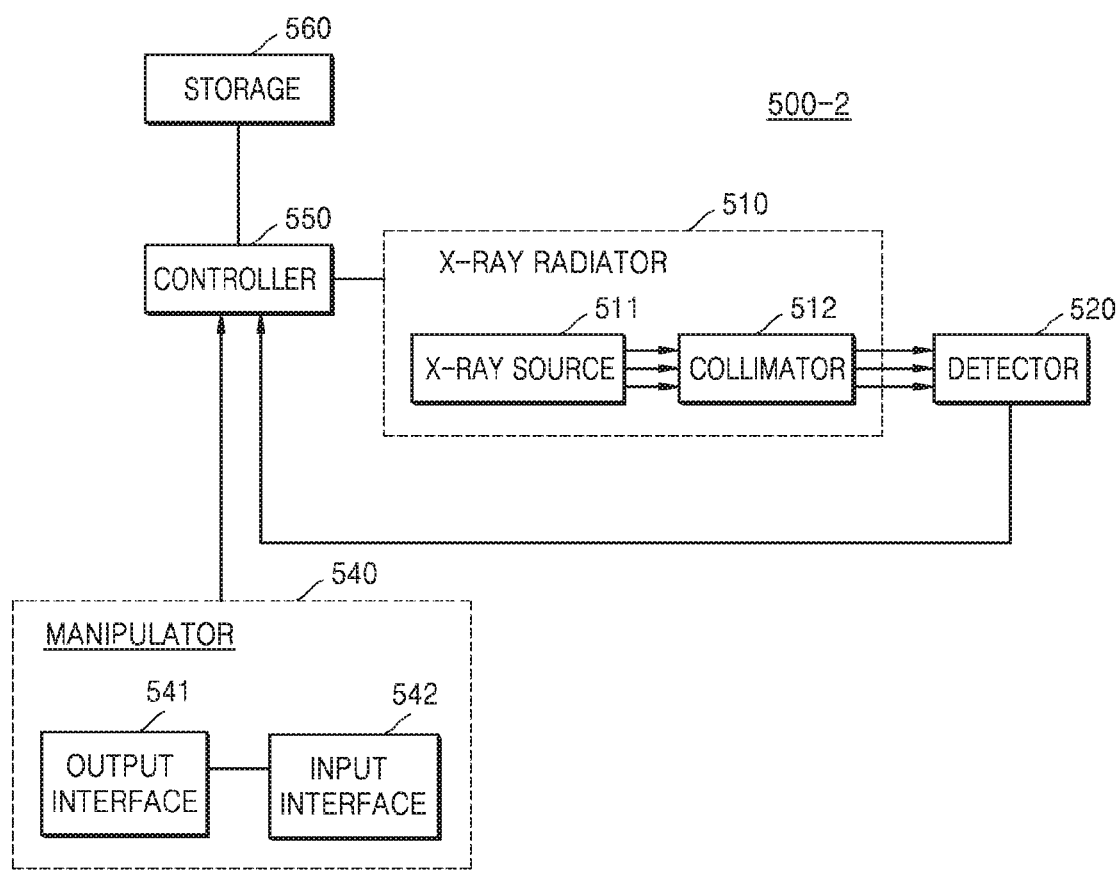
FIG. 14 is a block diagram of a configuration of an X-ray apparatus according to an embodiment.

FIG. 14 is a block diagram of a configuration of an X-ray apparatus 500-2 according to an embodiment. The X-ray apparatus 500-2 may further include a storage 560. Because components of the X-ray apparatus 500-2 other than the storage 560 respectively correspond to their counterparts of the X-ray apparatus 500 described with reference to FIG. 5, descriptions already provided with respect to FIG. 5 will be omitted below.

Referring to FIG. 14, the X-ray apparatus 500-2 according to the present embodiment may further include the storage 560 configured to store standard body dimension information of an object to be X-rayed.

The standard body dimension information may be information about sizes of body parts. In detail, the standard body dimension information may include a head size, a thickness of a thorax, a circumference of abdomen, a waist circumference, and sizes of hands and feet. According to an embodiment, standard body dimension information of an object may be classified for each body shape type with respect to at least one of a patient's age, height, and weight and stored in the storage 560. In detail, body shape information including a patient's head size, thorax thickness, width of abdomen, waist circumference, and hand and feet sizes may be classified along with at least one of a patient's age, height, and weight and stored in the storage 560.

The controller 550 may receive information about a standard body shape of the object from the storage 560 and determine the order of imaging operations with respect to a plurality of partial X-ray imaging regions. In detail, the controller 550 may acquire information of the object represented on each of the plurality of partial X-ray imaging regions based on information corresponding to an imaging area with respect to the standard body shape of the object, stored in the storage 560. For example, if the imaging area corresponds to parts from a head to an abdomen of the object, the controller 550 may acquire size information of the object represented on the plurality of partial X-ray imaging regions based on standard body dimension information about a head, a thorax, and an abdomen with respect to the standard body shape of the object, stored in the storage 560.

The controller 550 may determine, based on the acquired information, the order of imaging operations so that the imaging operations may be performed in the order from a partial X-ray imaging region where a portion of the object 10 having a greatest area is represented to a partial X-ray imaging region where a portion of the object 10 having a smallest area is represented. For example, if the object 10 is an adult man having an obese body shape type and information indicating that an abdomen has a greater area than that of a thorax is stored in the storage 560, the controller 550 may receive the information from the storage 560 and determine the order of imaging operations so that the imaging operations are performed for a partial X-ray imaging region where the abdomen is represented earlier than for a partial X-ray imaging region where the thorax is represented.

According to an embodiment, the manipulator 540 may receive a user input for inputting information about a body shape of the object 10 including a patient's age, height, and weight. The controller 550 may classify the object 10 as a predetermined type according to the user input received by the manipulator 540. The controller may classify the object 10 as the predetermined type according to a body shape of the object 10, provide information about the predetermined type to the storage 560, and acquire standard body dimension information about the predetermined type from the storage 560.

Figure 15:
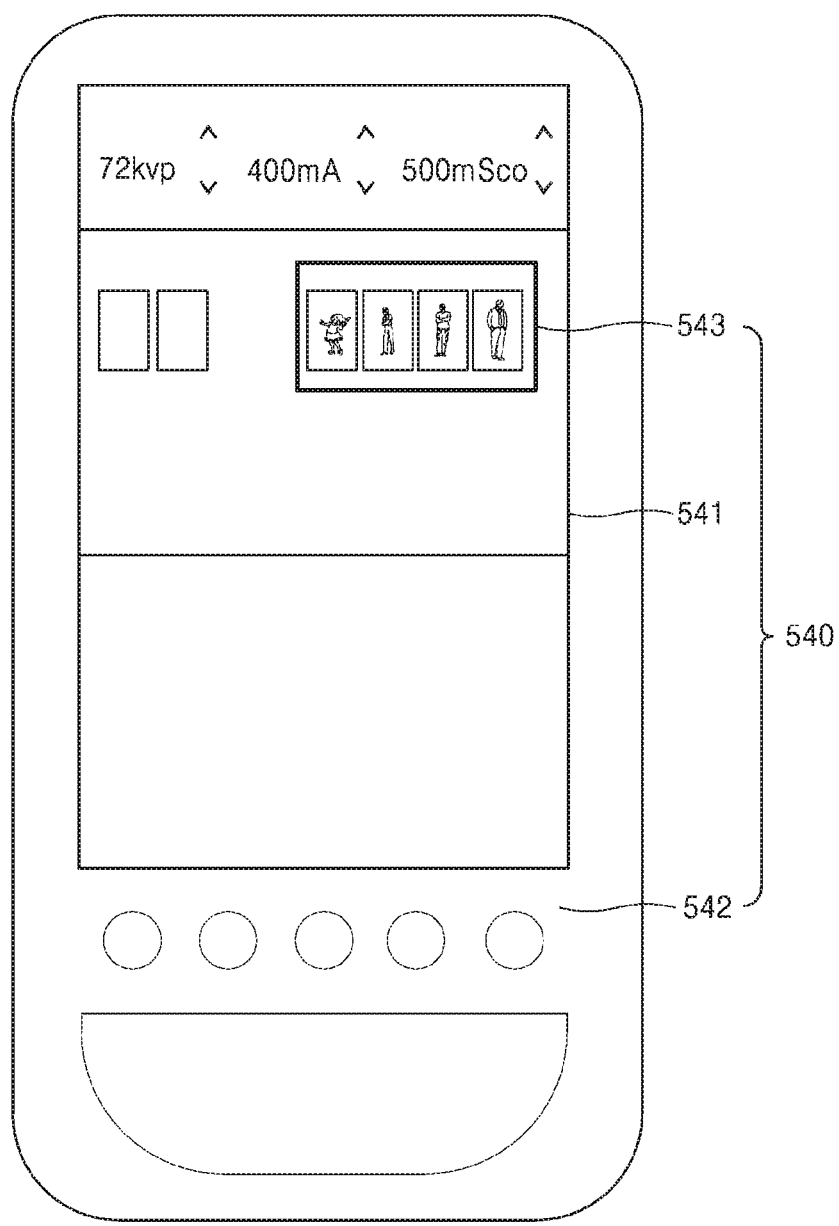
FIG. 15 is a diagram for explaining a method, performed by an X-ray apparatus, of performing partial imaging, according to an embodiment.

FIG. 15 is a diagram for explaining a method, performed by the X-ray apparatus 500-2, of performing partial imaging according to an embodiment.

Referring to FIG. 15, the manipulator 540 may include an output interface 541 and an input interface 542, and the output interface 541 may display a body shape information input user interface (UI) 543. The body shape information input UI 543 may be displayed on the output interface 541 and may be a UI configured to receive a user input for setting body shape information of the object.

Although FIG. 15 shows that the output interface 541 and the input interface 542 included in the manipulator 540 are separated from each other, embodiments are not limited thereto, and the input interface 542 or a part of the input interface 542 may be implemented in the output interface 541. For example, if the input interface 542 includes a touch screen, the touch screen may be included in the output interface 541.

The output interface 541 may further display information about an intensity of an X-ray, timing of radiation of an X-ray, etc.

The body shape information input UI 543 may receive a user input for inputting a body shape type of the object 10. In detail, the body shape information input UI 543 may receive a user input for inputting information about a patient's age, height, weight, etc. For example, the body shape information input UI 543 may display a UI configured to provide icons respectively representing a child, an adult, a thin body shape, an average body shape, and an obese body shape, etc., and select one from among the icons.

Figure 16:
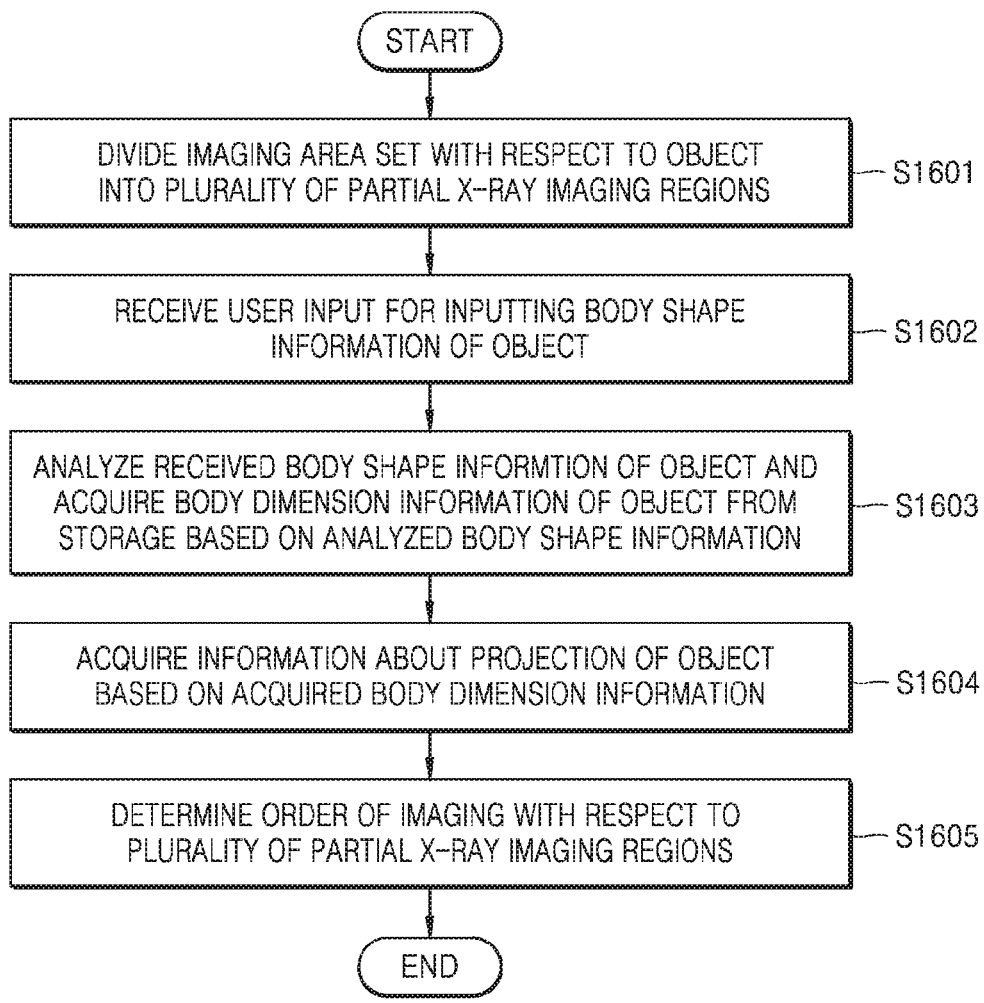
FIG. 16 is a flowchart of a method of performing partial imaging according to an embodiment.

FIG. 16 is a flowchart of a method of performing partial imaging according to an embodiment.

Referring to FIG. 16, an X-ray apparatus divides an X-ray imaging area with respect to the object 10 into a plurality of partial X-ray imaging regions (operation S1601). In detail, the input interface (542 of FIG. 14) may receive a user input for setting an X-ray imaging area with respect to the object 10. The controller 550 (550 of FIG. 14) may divide an X-ray imaging area set based on the user input received by the input interface 542 into a plurality of partial X-ray imaging regions.

The X-ray apparatus receives a user input for inputting a body shape type of the object 10, i.e., body shape information of the object 10 (operation S1602). The body shape type of the object 10 may be information related to data such as an age, height, and weight of the object 10. Alternatively, the body shape type of the object 10 may be of a child, an adult, a thin body shape, an average body shape, an obese body shape, or the like. According to an embodiment, the input interface 542 may also receive a user input for selecting one type from among a plurality of types into which the object 10 is classified according to body shape factors such as an age, height, and weight of the object 10 to be X-rayed, i.e., a specific patient. According to an embodiment, the manipulator 540 may include a body shape information input interface for displaying a UI configured to provide a plurality of types into which a patient is classified according to a patient's body shape. The manipulator 540 may receive a user input for selecting a type similar to that of the object 10 to be X-rayed from among the plurality of types provided by the UI displayed in the body shape information input interface.

The X-ray apparatus analyzes the received body shape information of the object 10 and acquire standard body dimension information of the object 10 based on the analyzed body shape information (operation S1603).

The X-ray apparatus obtains size information of the object 10 represented on the plurality of partial X-ray imaging regions based on the acquired standard body dimension information of the object 10, i.e., a patient (operation S1604).

The X-ray apparatus determines the order of imaging operations with respect to the plurality of partial X-ray imaging regions (operation S1605). According to an embodiment, the controller 550 may receive standard body shape information about areas of a head, a thorax, and an abdomen stored in the storage 560 and corresponding to a patient's body shape type and determine, based on the received standard body shape information, the order of imaging operations so that the imaging operations may be performed in the order from a partial X-ray imaging region where a portion of the object 10 having a greatest area is represented on a partial X-ray imaging region where a portion of the object 10 having a smallest area is represented.

The method of FIG. 16 may be performed by the X-ray apparatus 500-2 of FIG. 14.

Figure 17A:
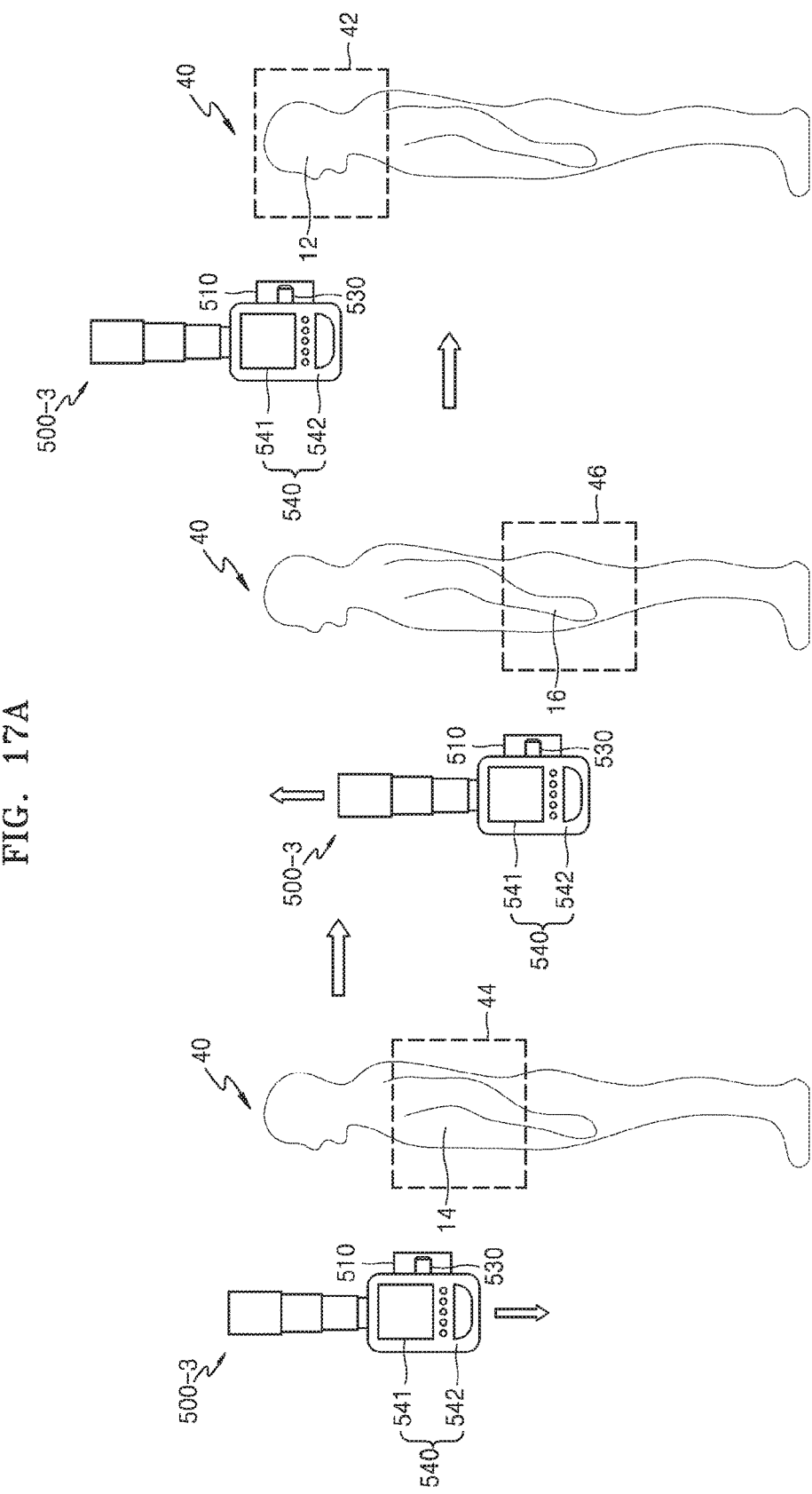
FIGS. 17A and 17B are diagrams for explaining a method, performed by an X-ray apparatus, of changing an order of partial imaging operations performed on an object, according to an embodiment.
Figure 17B:
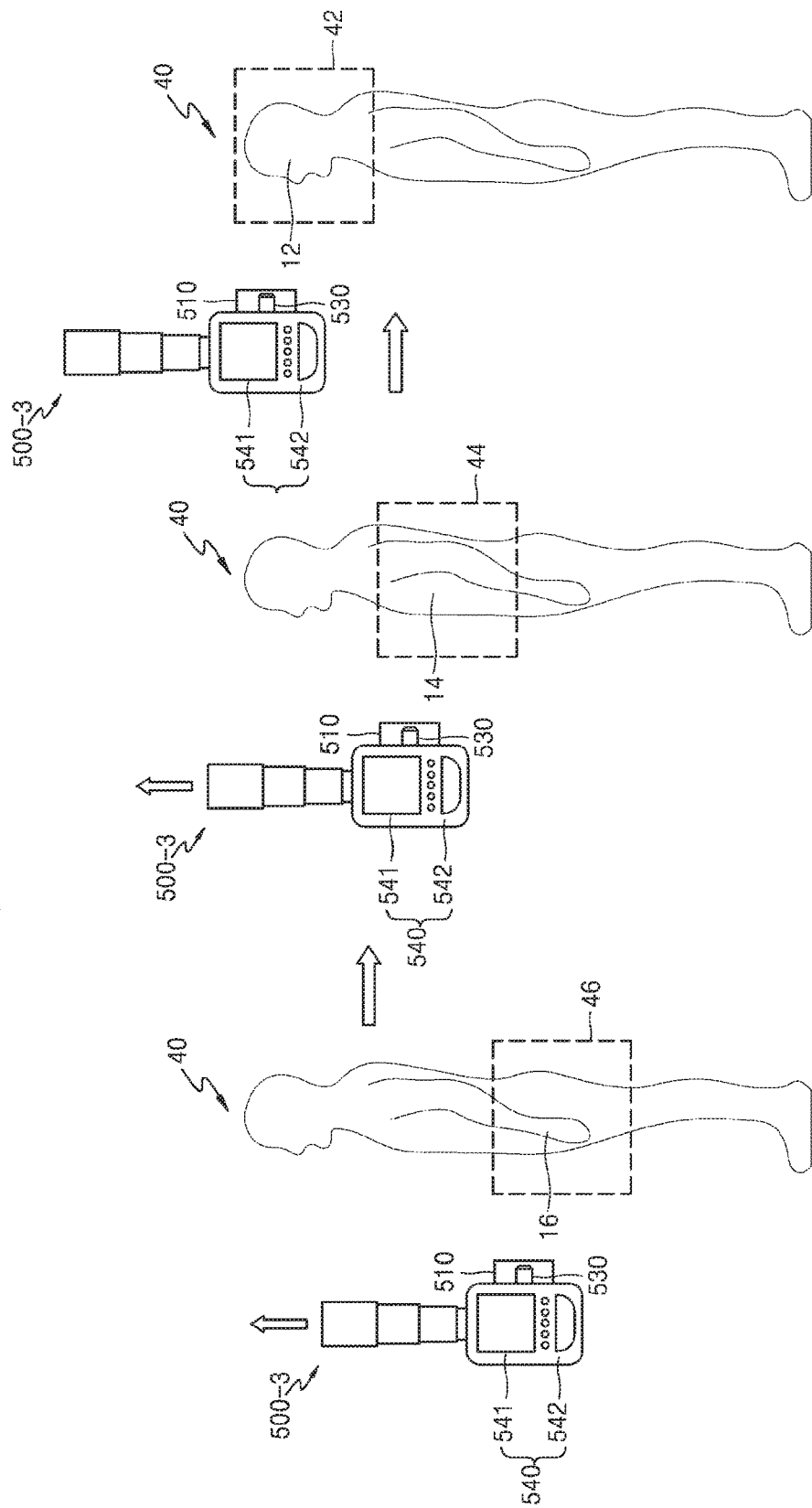

FIGS. 17A and 17B are diagrams for explaining a method, performed by an X-ray apparatus 500-3, of changing the order of partial imaging operations on an object 10, according to an embodiment. The X-ray apparatus 500-3 shown in FIGS. 17A and 17B operates in a different way than but may include the same components as the X-ray apparatus 500 described with reference to FIGS. 5 and 6. Thus, descriptions of the components of the X-ray apparatus 500-3 that are already provided with respect to their corresponding components of the X-ray apparatus 500 in conjunction with FIGS. 5 and 6 will be omitted below.

Referring to FIG. 17A, the X-ray apparatus 500-3 may include a controller configured to divide an X-ray imaging area of the object 40 into a plurality of partial X-ray imaging regions 42, 44, and 46 for which X-ray imaging of the object 40 is performed. The plurality of partial X-ray imaging regions 42, 44, and 46 may include first through third partial X-ray imaging regions 42, 44, and 46 where a skull 12, a thorax 14, and an abdomen 16 of the object 40 are respectively represented. The controller may determine the order of partial imaging operations according to the order from a partial X-ray imaging region where a portion of the object 40 having a greatest area is represented on a partial X-ray imaging region where a portion of the object 40 having a smallest area is represented. According to an embodiment, the controller may determine the order of imaging operations according to a descending order in terms of widths of portions of the object 40 respectively represented on the plurality of partial X-ray imaging regions 42, 44, and 46.

According to an embodiment, the controller may determine the order of imaging operations so that the imaging operations are performed in the order from the second partial X-ray imaging region 44 where the thorax 14 of the object 40 is represented on the third partial X-ray imaging region 46 where the abdomen 16 of the object 40 is represented on the first partial X-ray imaging region 42 where the skull 12 of the object 40 is represented. However, after irradiating X-rays onto the thorax 14 of the object 40, an X-ray radiator 510 is required to move downward to the abdomen 16 in order to irradiate X-rays onto the abdomen 16 of the object 40 and then move back upward toward the skull 12 past the thorax 14 in order to irradiate X-rays onto the skull 12. In other words, when the order of imaging operations with respect to the plurality of partial X-ray imaging regions 42, 44, and 46 are determined only based on an area of width of the object 40 represented thereon, paths of movement of the X-ray radiator 510 may overlap each other, and thus the total partial X-ray imaging time may be increased. The increase in total partial X-ray imaging time may cause after-images or ghost images to appear as the object 40 moves.

Referring to FIG. 17B, the controller of the X-ray apparatus 500-3 may determine the order of imaging operations with respect to the plurality of partial X-ray imaging regions 42, 44, and 46 based on areas and widths of portions of the object 40 respectively represented on the plurality of partial X-ray imaging regions 42, 44, and 46 and a path of movement of the X-ray radiator 510. According to an embodiment, when a difference between areas of portions of the object 40 respectively represented on the plurality of partial X-ray imaging regions 42, 44, and 46 is less than or equal to a predetermined threshold value, the controller may change the order of imaging operations determined based on areas of portions of the object 40 respectively represented on the plurality of partial X-ray imaging regions 42, 44, and 46. In this case, the X-ray radiator 510 may move in a first direction to be opposite each portion of the object 40 only once. By determining the order of imaging operations with respect to the plurality of partial X-ray imaging regions 42, 44, and 46 so as not to change the direction of movement of the X-ray radiator 510, a length of a path of movement of the X-ray radiator 510 may be minimized.

For example, if the thorax 14 of the object 40 represented on the second partial X-ray imaging region 44 has a greater area than that of the abdomen 16 of the object represented on the third partial X-ray imaging region 46 and if a difference between areas of portions of the object 40 respectively represented on the second and third partial X-ray imaging regions 44 and 46 is less than or equal to a predetermined threshold value, the controller may determine the order of imaging operations so that the imaging operations are performed first for the third partial X-ray imaging region 46 and then for the second partial X-ray imaging region 44.

According to an embodiment, the X-ray apparatus 500-3 may determine the order of imaging operations with respect to partial X-ray imaging regions by taking into account size information of the object 40 and a direction of movement of the X-ray radiator 510. Thus, partial imaging time may be reduced and movement of the object 40 may be minimized, thereby suppressing generation of after-images and ghost images.

Figure 18:
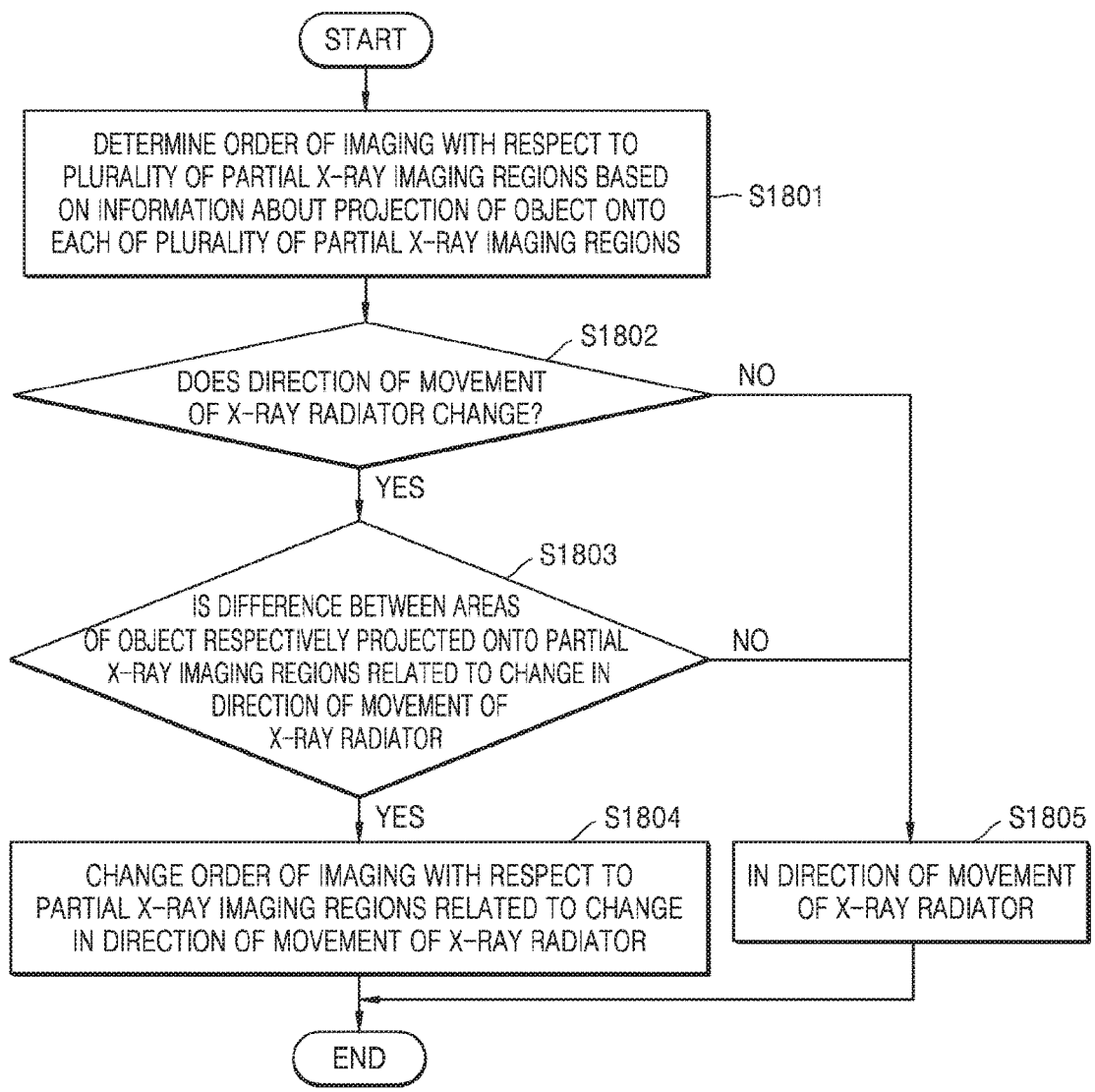
FIG. 18 is a flowchart of a method, performed by an X-ray apparatus, of performing partial imaging operations, according to an embodiment.

FIG. 18 is a flowchart of a method, performed by an X-ray apparatus, of performing partial imaging operations according to an embodiment.

The X-ray apparatus determines the order of imaging operations with respect to the plurality of partial X-ray imaging regions (42, 44, and 46 of FIGS. 17A and 17B) based on the size information of the object 40 represented on the plurality of partial X-ray imaging regions 42, 44, and 46 (operation S1801).

The X-ray apparatus detects whether there is a change in a direction of movement of the X-ray radiator (510 of FIGS. 17A and 17B) (operation S1802). According to an embodiment, the X-ray radiator 510 may move in the first direction to be opposite and pass each portion of the object 40 only once (See FIG. 17B). According to an embodiment, the X-ray radiator 510 may move in the first direction and change its direction to a second direction (See FIG. 17A) that is opposite to the first direction. In this case, the X-ray radiator 510 may be opposite a portion of the object 40 to pass it two or more times.

The X-ray apparatus may detect a difference between areas of portions of the object 40 respectively represented on partial X-ray imaging regions related to the change in the direction of movement of the X-ray radiator 510 from among the plurality of partial X-ray imaging regions 42, 44, and 46 and compare the difference to a predetermined threshold value for analysis (operation S1803). According to an embodiment, the controller 550 may determine whether a difference between areas of portions of the object 40 respectively represented on partial X-ray imaging regions related to a change in a direction of movement of the X-ray radiator 510 is less than or equal to a threshold value.

In one embodiment, the threshold value may be a value that is in a range of 0% to 20% of a greater one of areas of portions of the object 40 respectively represented on partial X-ray imaging regions related to a change in a direction of movement of the X-ray radiator 510 from among the plurality of partial X-ray imaging regions 42, 44, and 46. In an embodiment, the threshold value may be a value that is in a range of 0% to 20% of a greater one of widths of portions of the object 40 respectively represented on partial X-ray imaging regions related to a change in a direction of movement of the X-ray radiator 510.

The X-ray apparatus changes the order of imaging operations with respect to the partial X-ray imaging regions related to a change in the direction of movement of the X-ray radiator 510 (operation S1804). According to an embodiment, when a difference between widths of portions of the object 40 respectively represented on the second and third partial X-ray imaging regions 44 and 46 is less than or equal to the threshold value, the controller 550 may change the order of imaging operations so that the imaging operations are performed first for the third partial X-ray imaging region 46 and then for the second partial X-ray imaging region 44 (See FIG. 17B).

When the difference between the areas of the portions of the object 40 respectively represented on the partial X-ray imaging regions related to a change in the direction of movement of the X-ray radiator 510 is greater than the predetermined threshold value, the X-ray apparatus may perform the imaging operations with respect to the plurality of partial X-ray imaging regions 42, 44, and 46 according to the order determined in operation S1801 (operation S1805).

The method of FIG. 18 may be performed by the X-ray apparatus 500-3 of FIGS. 17A and 17B.

Figure 19:
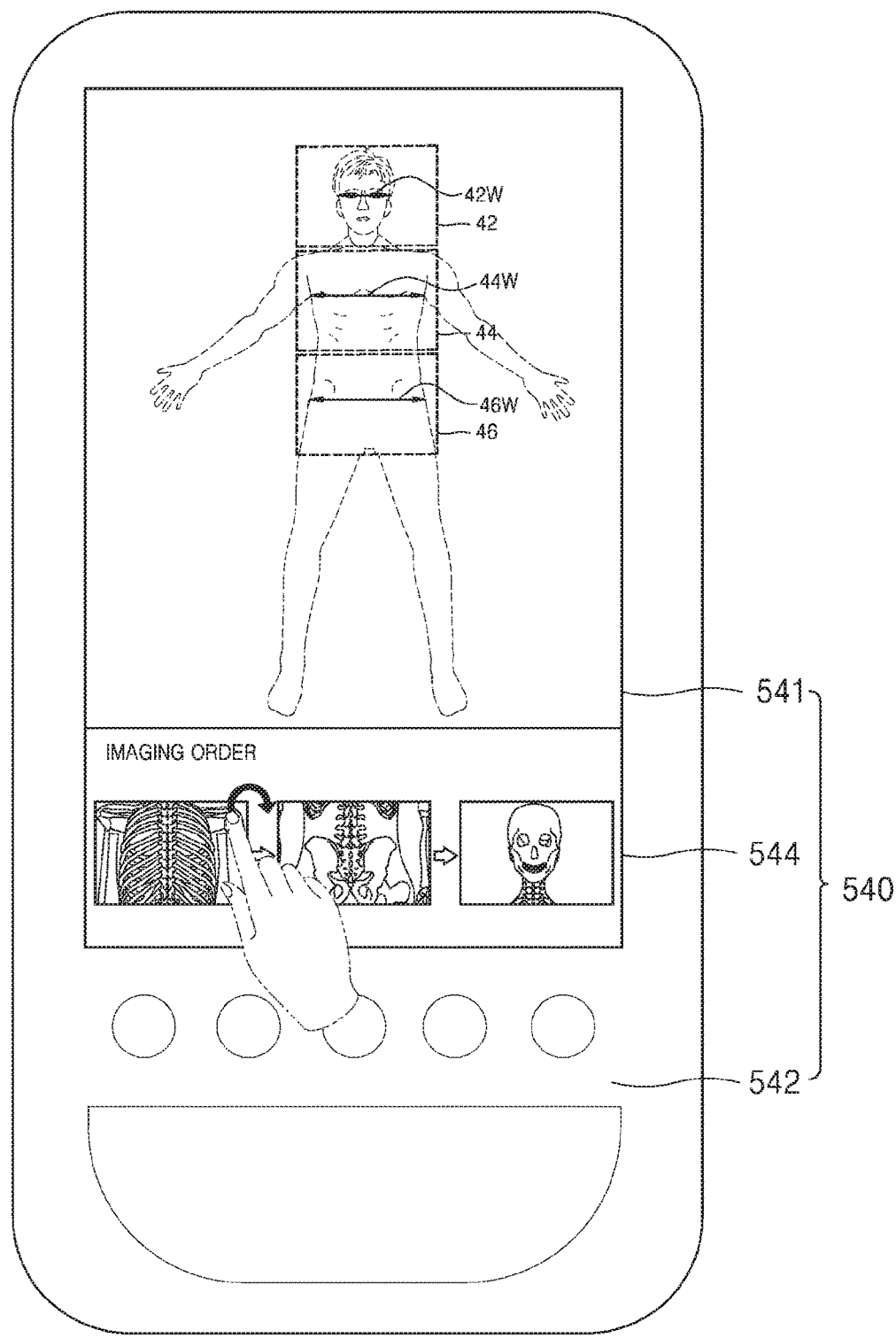
FIG. 19 is a diagram for explaining a method, performed by an a X-ray apparatus, of changing an order of partial imaging operations, according to an embodiment.

FIG. 19 is a diagram for explaining a method, performed by the X-ray apparatus 500-3, of changing the order of partial imaging operations according to an embodiment.

Referring to FIG. 19, a manipulator 540 may include an output interface 541 and an input interface 542.

The output interface 541 outputs an imaging order changing UI 544 for setting the order of partial imaging operations onto a screen.

According to an embodiment, the output interface 541 may be a touch screen configured to display a UI and receive a user's touch input. The output interface 541 may display a plurality of partial X-ray imaging regions 42, 44, and 46 and an object 40 represented on each of the plurality of partial X-ray imaging regions 42, 44, and 46. The output interface 541 may display a photographic image obtained by photographing the object 40 via an image acquisitioner (530 of FIGS. 17A and 17B). In an embodiment, the output interface 541 may display widths 42W, 44W, and 46W of portions of the object 40 respectively represented on the plurality of partial X-ray imaging regions 42, 44, and 46. In an embodiment, the output interface 541 may display areas of portions of the object 40 respectively represented on the plurality of partial X-ray imaging regions 42, 44, and 46.

The imaging order changing UI 544 may arrange and display the plurality of partial X-ray imaging regions 42, 44, and 46 according to the order of imaging operations determined by the controller 550. The order of imaging operations with respect to the plurality of partial X-ray imaging regions 42, 44, and 46 may be determined based on information about portions of the object 40 respectively represented on the plurality of partial X-ray imaging regions 42, 44, and 46, such as areas or widths of the portions of the object 40, or be determined as being the order that minimizes a length of a path of movement of the X-ray radiator 510.

According to an embodiment, the imaging order changing UI 544 may be implemented as a graphical user interface (GUI) configured to graphically display the plurality of partial X-ray imaging regions 42, 44, and 46. The imaging order changing UI 544 may receive a user input for changing the order of imaging operations by selecting one from among a plurality of partial X-ray imaging regions 42, 44, and 46 and touching and swiping the selected one. According to an embodiment, by providing a UI such as the imaging order changing UI 544 configured to receive a user input for changing the imaging order instead of determining the order of imaging operations with respect to the plurality of partial X-ray imaging regions 42, 44, and 46 only based on information of portions of the object 40 respectively represented thereon, it is possible to shorten the partial X-ray imaging time and prevent generation of after-images and ghost images.

Figure 20:
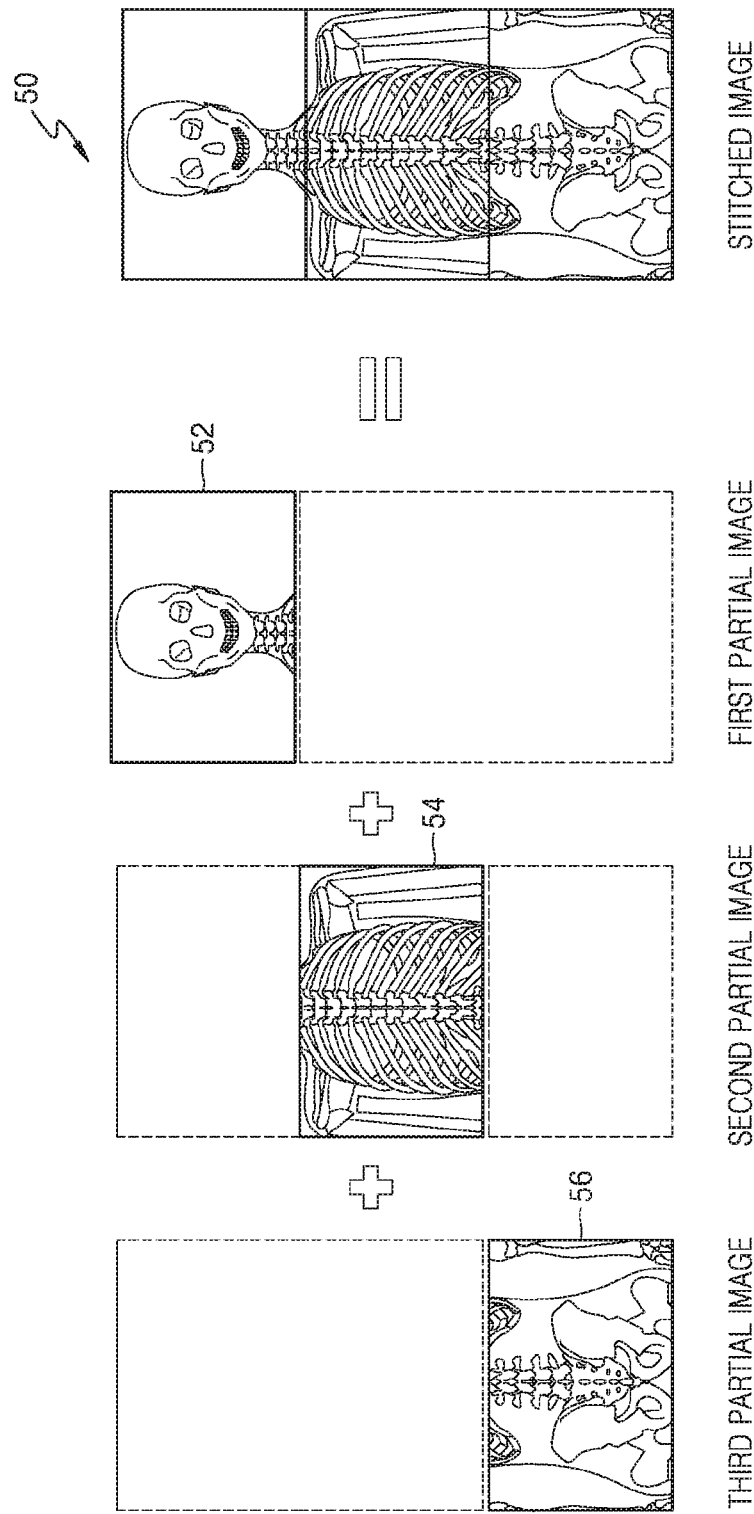
FIG. 20 is a diagram for explaining an example of obtaining an X-ray image by stitching together a plurality of partial images acquired using an X-ray apparatus.

FIG. 20 is a diagram for explaining an example of obtaining an X-ray image by stitching together a plurality of partial images acquired using the X-ray apparatus 500, 500-1, 500-2, or 500-3.

Referring to FIG. 20, the plurality of partial images may include a third partial image 56 that is a partial X-ray image of a portion including an abdomen of the object 50, a second partial image 54 that is a partial X-ray image of a portion including a thorax of the object 50, and a first partial image 52 that is a partial X-ray image of a portion including a skull of the object 50. An X-ray image 50 may be obtained by stitching together the first through third partial images 52, 54, and 56. Stitching is an image processing technique for combining the plurality of partial images 52, 54, and 56 into the single X-ray image 50. According to an embodiment, if the plurality of partial images 52, 54, and 56 respectively have overlapping portions therebetween, stitching may be an image processing technique for detecting the overlapping portions and combining the overlapping portions together.

The stitching may be performed by the controller 550 included in the X-ray apparatus 500, 500-1, 500-2, or 500-3.

Figure 21:
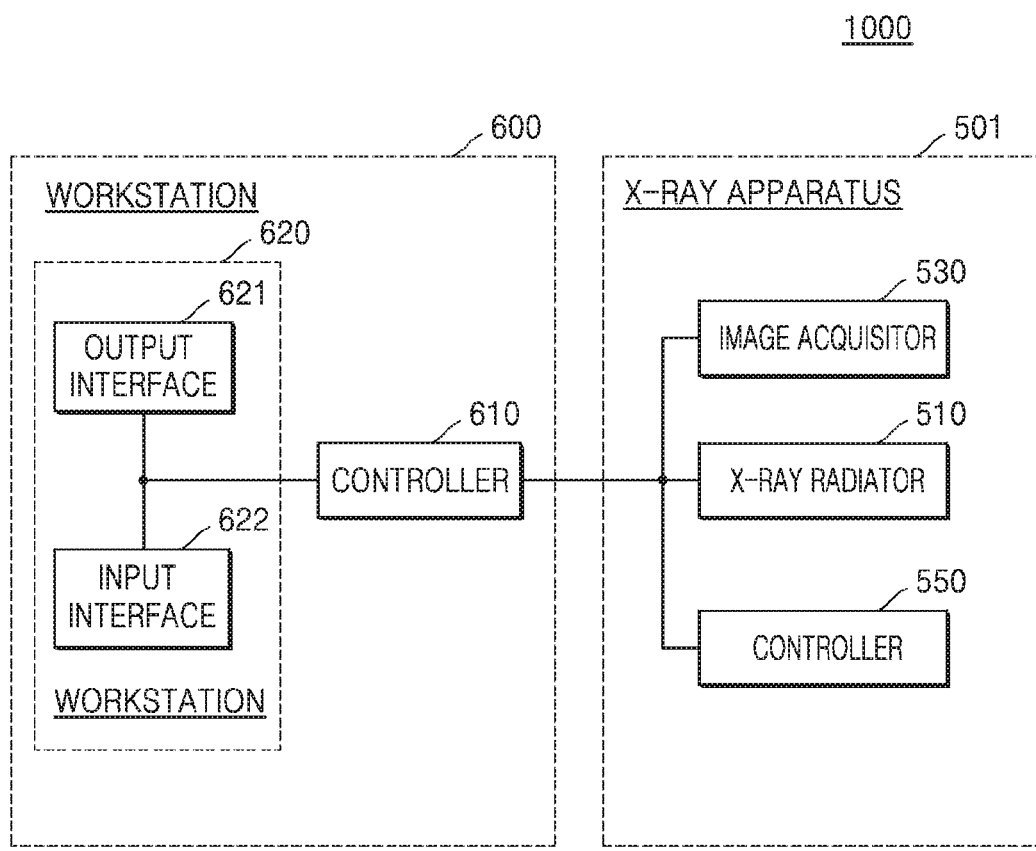
FIG. 21 illustrates an X-ray system according to an embodiment.

FIG. 21 illustrates an X-ray system 1000 according to an embodiment.

Referring to FIG. 21, the X-ray system 1000 according to the present embodiment may include an X-ray apparatus 501 and a workstation 600.

The X-ray apparatus 501 may include an X-ray radiator 510, an image acquisitioner 530, and a controller 550. Because the X-ray apparatus 501 may include the same components as their counterparts of the X-ray apparatus 500 shown and described with reference to FIGS. 5 and 6, descriptions already provided with respect to FIGS. 5 and 6 will be omitted here. Furthermore, the X-ray apparatus 501 may include the image acquisitioner 530, and because the image acquisitioner 530 corresponds to the image acquisitioner 530 shown and described with reference to FIG. 9, a detailed description thereof will be omitted below.

The workstation 600 may include a controller 610 and a manipulator 620 for providing a UI. The manipulator 620 may include an output interface 621 and an input interface 622. The descriptions with respect to the manipulators 540 included in the X-ray apparatuses 500, 500-1, 500-2, and 500-3 respectively shown and described with reference to FIGS. 5, 9, 14, and FIGS. 17A and 17B may apply to the manipulator 620 included in the workstation 600. The UI provided in the manipulator 620 of the workstation 600 may be the same as the UIs provided in the manipulators 540 in the X-ray apparatuses 500, 500-1, 500-2, and 500-3. Thus, a simple, intuitive UI may be provided, thereby allowing the user to intuitively and conveniently manipulate or control the X-ray apparatuses 500, 500-1, 500-2, and 500-3.

The image acquisitioner 530 of the X-ray apparatus 501 may acquire a photographic image of the object 50 by photographing the object 50.

The output interface 621 of the workstation 600 may display the acquired image. The input interface 622 may receive start point setting information for setting a start point of an area where X-ray imaging is to be performed in the acquired image from the user.

The output interface 621 may display portions of the object 50 respectively represented on at least one partial X-ray imaging region on the photographic image. According to an embodiment, the manipulator 620 may include an imaging order changing UI.

The controller 610 may divide an X-ray imaging area set according to a user input into a plurality of partial X-ray imaging regions and determine the order of imaging operations with respect to the plurality of partial X-ray imaging regions based on the size information of the object 50 represented on the plurality of partial X-ray imaging regions.

According to an embodiment, the controller 610 may determine the order of imaging operations based on areas of portions of the object 50 respectively represented on the plurality of partial X-ray imaging regions. The controller 610 may determine the order of imaging operations according to the order from a partial X-ray imaging region where a portion of the object 50 having a large area is represented on a partial X-ray imaging region where a portion of the object 50 having a small area is represented.

Furthermore, the controller 610 may determine the order of imaging operations according to the order from a partial X-ray imaging region where a portion of the object 50 having a large width is represented on a partial X-ray imaging region where a portion of the object 50 having a small width is represented.

Furthermore, the controller 610 may determine the order of imaging operations with respect to the plurality of partial X-ray imaging regions based on the photographic image provided by the image acquisitioner 530. According to an embodiment, the controller 610 may determine, based on the photographic image provided by the image acquisitioner 530, the order of imaging operations according to the order from a partial X-ray imaging region where a portion of the object 50 having a greatest area is represented on a partial X-ray imaging region where a portion of the object 50 having a smallest area is represented.

Furthermore, the controller 610 may receive standard body shape information of the object 50 from a storage (not shown) included in the X-ray apparatus 501 and determine the order of imaging operations with respect to the plurality of partial X-ray imaging regions Furthermore, when a difference between areas of portions of the object 50 respectively represented on the plurality of partial X-ray imaging regions is less than or equal to a predetermined threshold value, the controller 610 may change the order of imaging operations determined based on areas of portions of the object 50 respectively represented on the plurality of partial X-ray imaging regions.

Furthermore, when a user input for changing the order of imaging operations determined based on areas of portions of the object 50 respectively represented on the plurality of partial X-ray imaging regions is received from the input interface 622, the controller 610 may change the order of the imaging operations with respect to the plurality of partial X-ray imaging regions based on the received user input.

As described above, according to an embodiment, an X-ray apparatus and system capable of preventing generation of after-images and ghost images due to partial X-ray imaging may be provided. According to an embodiment, an intuitive UI for controlling the X-ray apparatus and system may be provided to offer convenience for users of the X-ray apparatus and system.

The above-described embodiments of the present disclosure may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.), and transmission media such as Internet transmission media.

While the present disclosure has been particularly shown and described with reference to embodiments thereof, it will be understood by those of ordinary skill in the art that various changes in form and details may be made therein without departing from the spirit and scope of the present disclosure as defined by the following claims.

What is claimed is:

1. An X-ray apparatus comprising:
an input interface configured to receive a first user input for setting an imaging area of an object;
a controller configured to divide the set imaging area into a plurality of partial X-ray imaging regions and determine an order of imaging operations for the plurality of partial X-ray imaging regions based on size information about portions of the object respectively represented on the plurality of partial X-ray imaging regions; and
an X-ray radiator configured to radiate X-rays onto the plurality of partial X-ray imaging regions according to the determined order of imaging operations to perform partial imaging of the object.

2. The X-ray apparatus of claim 1, wherein the controller determines the order of the imaging operations to be from a partial X-ray imaging region among the plurality of partial X-ray imaging regions having a portion of the object with a large area or width to a partial X-ray imaging region among the plurality of partial X-ray imaging regions having a portion of the object having a small area or width.

3. The X-ray apparatus of claim 2, wherein the controller acquires at least one of representative values including an average value, a minimum value, a median value, and a maximum value of widths of a portion of the object represented on each of the plurality of partial X-ray imaging regions and determines the order of the imaging operations for the plurality of partial X-ray imaging regions based on the acquired at least one of the representative values.

4. The X-ray apparatus of claim 3, wherein the controller measures the widths of the portion of the object represented on each of the plurality of partial X-ray imaging regions at predetermined sampling intervals arranged in a vertical direction and acquires a representative value of widths in a horizontal direction of the object based on the measured widths of the portion of the object.

5. The X-ray apparatus of claim 2, further comprising an image acquisitioner configured to acquire a photographic image by photographing the object,
wherein the controller acquires the size information about the portions of the object respectively represented on the plurality of partial X-ray imaging regions, based on the acquired photographic image.

6. The X-ray apparatus of claim 1, further comprising a storage configured to store standard body dimension information of the object comprising information about widths of the portions of the object,
wherein the controller acquires information about the widths of the portions of the object respectively represented on the plurality of partial X-ray imaging regions based on the stored standard body dimension information of the object and determines the order of the imaging operations for the plurality of partial X-ray imaging regions based on the acquired information.

7. The X-ray apparatus of claim 1, wherein the controller determines the order of the imaging operations for the plurality of partial X-ray imaging regions based on a size of areas of the portions of the object respectively represented on the plurality of partial X-ray imaging regions and a path of movement of the X-ray radiator.

8. The X-ray apparatus of claim 7, wherein the controller detects a change in a direction of movement of the X-ray radiator, determines, when the change in the direction of movement of the X-ray radiator is detected, whether a difference between areas of portions of the object respectively represented on partial X-ray imaging regions related to the change in the direction of movement of the X-ray radiator from among the plurality of partial X-ray imaging region is less than or equal to a threshold value, and changes the order of the imaging operations for the partial X-ray imaging operations if the difference is less than or equal to the threshold value.

9. The X-ray apparatus of claim 1, further comprising an output interface configured to display information representing the determined order of the imaging operations for the plurality of partial X-ray imaging regions,
wherein the input interface receives a second user input for approving or changing the determined order of the imaging operations,
wherein the controller re-determines the order of the imaging operations for the plurality of partial X-ray imaging regions based on the second user input.

10. The X-ray apparatus of claim 1, wherein the controller obtains an X-ray image of the object by stitching together a plurality of partial X-ray images acquired by performing the imaging operations in the determined order.

11. A method comprising:
receiving a first user input for setting an imaging area of an object;
dividing the set imaging area input into a plurality of partial X-ray imaging regions; and
determining an order of imaging operations for the plurality of partial X-ray imaging regions based on size information about portions of the object respectively represented on the plurality of partial X-ray imaging regions.

12. The method of claim 11, wherein the determining of the order of the imaging operations comprises determining the order of imaging operation to be from a partial X-ray imaging region among the plurality of partial X-ray imaging regions having a portion of the object with a large area or width to a partial X-ray imaging region among the plurality of partial X-ray imaging regions having a portion of the object having a small area or width.

13. The method of claim 12, wherein the determining of the order of the imaging operations comprises:
acquiring at least one of representative values including an average value, a minimum value, a median value, and a maximum value of widths of a portion of the object represented on each of the plurality of partial X-ray imaging regions; and
determining the order of the imaging operations for the plurality of partial X-ray imaging regions based on the acquired at least one of the representative values.

14. The method of claim 13, wherein the widths of the portion of the object represented on each of the plurality of partial X-ray imaging regions are measured at predetermined sampling intervals arranged in a vertical direction, and the representative value is acquired based on the measured widths of the portion of the object.

15. The method of claim 12, wherein the determining of the order of the imaging operations comprises acquiring information about areas of the portions of the object respectively represented on the plurality of partial X-ray imaging regions by photographing the object and determining the order of the imaging operations for the plurality of partial X-ray imaging regions based on the acquired information.

16. The method of claim 11, wherein the determining of the order of the imaging operations comprises acquiring standard body dimension information of the object comprising information about widths of the portions of the object and determining the order of the imaging operations for the plurality of partial X-ray imaging regions based on the acquired standard body dimension information.

17. The method of claim 11, wherein the determining of the order of the imaging operations comprises determining the order of imaging operations for the plurality of partial X-ray imaging regions based on a size of areas of the portions of the object respectively represented on the plurality of partial X-ray imaging regions and a direction of movement of an X-ray radiator configured to radiate X-rays onto the plurality of partial X-ray imaging regions in order to perform partial imaging of the object.

18. The method of claim 17, wherein the determining of the order of the imaging operations comprises:

detecting a change in a direction of movement of the X-ray radiator;

determining, when the change in the direction of movement of the X-ray radiator is detected, whether a difference between areas of portions of the object respectively represented on partial X-ray imaging regions related to the change in the direction of movement of the X-ray radiator from among the plurality of partial X-ray imaging region is less than or equal to a threshold value; and changing the order of the imaging operations for the partial X-ray imaging operations if the difference is less than or equal to the threshold value.

19. The method of claim 11, further comprising:

displaying the determined order of the imaging operations on an output interface;

receiving a second user input for approving or changing the determined order of the imaging operations displayed on the output interface; and re-determining the order of the imaging operations for the plurality of partial X-ray imaging regions based on the second user input.

20. A non-transitory computer-readable recording medium having recorded thereon a program for executing the method of claim 11 on a computer.

* * * * *